United States Patent [19]

Prusiner et al.

[11] Patent Number: 5,891,641
[45] Date of Patent: Apr. 6, 1999

[54] ASSAY FOR DISEASE RELATED CONFORMATION OF A PROTEIN

[75] Inventors: Stanley B. Prusiner, San Francisco; Jiri G. Safar, Concord, both of Calif.

[73] Assignee: The Regents of the University of California, Oakland, Calif.

[21] Appl. No.: 804,536

[22] Filed: Feb. 21, 1997

[51] Int. Cl.$^6$ .................. G01N 33/53; G01N 33/566; G01N 33/537; G01N 33/543
[52] U.S. Cl. .................. 435/7.1; 435/960; 435/961; 436/501; 436/518; 436/538; 436/542
[58] Field of Search ............ 435/7.1, 960, 961; 436/501, 518, 538, 542

[56] References Cited

U.S. PATENT DOCUMENTS

| | | | |
|---|---|---|---|
| 4,806,627 | 2/1989 | Wisniewski et al. | 530/387 |
| 5,565,186 | 10/1996 | Prusiner et al. | 424/9.2 |

FOREIGN PATENT DOCUMENTS

| | | | |
|---|---|---|---|
| WO 93/10227 | 5/1995 | WIPO. | |
| WO 97/43649 | 11/1997 | WIPO | G01N 33/68 |

OTHER PUBLICATIONS

Anderson et al., (1996) "Transmission dynamics and epidemiology of BSE in British cattle," *Nature* 382 ; 779–88.
Barry, R.A., et ., (1986) "Monoclonal Antiobiodies to the Cellular and Scrapie Prion Proteins," *Journal of Infectious Diseases* 154:518–521.
Basler et al., (1986)"Scrapie and Cellular PrP Isoforms Are Encoded by the Same Chromosomal Gene," *Cell* 46: 417–28.
Bode et al., (1985) "Characterization of Antisera Against Scrapie–Associated Fibrils (SAF) form Affected Hamster and Cross–Reactivity with SAF from Scrapie–Affected Mice and from Patients with Creutzfeldt–Jacob Disease," *J. Gen. Virol.* 66 (pt 11):2471–8.
Bolton et al., (1982)"Identification of a Protein That Purifies with the Scrapie Prion," *Science* 218:1309–11.
Brown et al., (1992) "Friendly Fire' in Medicine: Hormones, Homografts, and Creutzfeldt–Jakob Disease," *Lancet* 340:24–27.
Buchanan et al., (1991)"Mortality, Neoplasia, and Creutzfeldt–Jakob Disease in Patients Treated with Human Pituitary Growth Hormone in the United Kingdom", *BMJ* 302:824–828.
Bueler et al., (1992) "Normal Development and Behavior of Mice lacking the Neuronal Cell–surface PrP Protein," *Nature* 356:577–582.
Carter, et al., (1992) "High Level *Escherichia coli* Expression and Production of a Bivalent Humanized Antibody Fragment," *Biotechnology* 10:163–7.
Cochius et al., (1992) "Creutzfeldt–Jakob Disease in a Recipient of Human Pituitary–Derived Gonadotrophin: A Second Case," *J. Neurol. Neurosurg. Psychiatry* 55:1094–1095.
Cochius et al., (1990) "Creutzfeldt–Jakob Disease in a Recipient of Human Pituitary–Derived Gonadotrophin," *Aust. N.Z. J. Med.* 20:592–593.
Colling, et al., (1996) "Prion protein gene analysis in new variant cases of Creutzfeldt–Jakob disease," *Lancet* 348: 56.
Gajdusek, D.C. (1977) "Unconventional Viruses and the Origin and Disapperance of Kuru," *Science* 197:943–960.
Gibbs, Jr. et al., (1993) "Creutzfeldt–Jakob Disease Infectivity of Growth Hormone Derived form Human Pituitary Glands," *N. Engl. J. Med.* 328:358–359.
Goldfarb et al., (1992) "Fatal Familial Insomnia and Familial Creutzfeldt–Jakob Disease: Disease Phenotype Determined by a DNA Polymorphism," *Science* 258:806–808.
Healy et la., "Creutzfeldt–Jakob Disease After Pituitary Gonadotrophins: The Prion is the PRoblem," *BMJ* (1993) 307:517–518.
Hsaio et al., (1996) "Serial transmission in rodents of neurodegeneration from transgenic mice expressing mutant rion protein," *Proc. National Acad. Sci. USA* 91:9126–30.
Kascsak, R.J., et al., (1987) "Mouse Polyclonal and Monoclonal Antibody to Scrapie–Associated Fibril Proteins" *Journal of Virology* 61:3688–3693.
Lasmezas et al., (1993) "Recombinant Human Growth Hormone and Insulin–Like Growth Factor I Induce PRP Gene Expression in PC12 Cell," *Biochem. Biophys. Res. Commun.* 196:1163–1169.
McKinley et al., (1983) "A Protease–Resistant Protein is a Structural Component of the Scrapie Prion," *Cell* 35:57–62.
Mehlhorn et al., (1996) "High–Level Expression and Characterization of a Purified 142–Residue Polyepetide of the Prion Protein," *Biochemistry* 35: 5528–37.
Meyer et al., (1986) "Separation and Properties of Cellular and Scrapie Prion Proteins," *Proc. Natl. Acad. Sci. USA* 83: 3693–7.

(List continued on next page.)

Primary Examiner—Michael P. Woodward
Assistant Examiner—Mary K. Zeman
Attorney, Agent, or Firm—Karl Bozicevic; Bozicevic & Reed LLP

[57] ABSTRACT

An assay method is disclosed which makes it possible to determine the presence of a diseased related conformation of a protein (e.g., PrP$^{Sc}$) in a sample. A sample is divided into two portions and the first portion is cross-linked to a first solid support and then contacted with a labelled antibody which binds to a non-disease form of the protein with a higher degree of affinity (e.g, 4 to 30 fold higher) than to the disease form of the protein. The second portion is treated in a manner which causes any disease form of the protein to change conformation to a form with a higher binding affinity for the labelled antibody. The treated second portion is then bound to a second solid support and contacted with labelled antibody. The level of labelled antibody binding to a protein in the first and second portions is determined and the amounts measured in each are compared. The difference between the two measurements is an indication of whether the diseased related conformation of the protein was present in the sample.

20 Claims, 6 Drawing Sheets

U.S. PATENT DOCUMENTS

Oesch, et al., (1985) "A Cellular Gene Encodes a Scrapie PrP 27–30 Protein," *Cell 40*: 735–46.

Pan, et al., (1993) "Conversion of α–helices into β–sheets features in the fomation of the scrapie prion proteins," *Proc. Natl. Acad. Sci. USA*, 10962–66.

Prusiner, S.B., et al., (1983) "Scrapie prions aggregate to form amyloid–like birefringent rods," *Cell 35*: 349–58.

Prusiner, S.B. et al., "Biology of Prions," *The Molecular and Genetic Basis of Neurological Disease*, 2nd Edition, Chap. 7, pp. 103–143.

Rogers et al., (1991) "Epitope Mapping of the Syrian Hamster Prion Protein Using Chimeric and Mutant Genes in a Vaccinia Virus Expression System," *J. Immunol. 147*: 3568–74.

Rogers, et al., (1993) "Conversion of truncated and elongated prion proteins into the scrapie isoform in cultured cells," *Proc. Natl. Acad. Sci. USA 90*:3182–6.

Safar et al. *J.*, (1993) "Conformational Transitions, Dissociation, and Unfolding of Scrpie Anyloid (Prion) Protein," *Biol. Chem. 268*: 20276–84.

Safar, et al., (1990) "Scrapie–associated precursor proteins: Antigenic relationship between species and immunocytochemical localization in normal, scrapie, and Creutzfeldt-Jakob disease brains," *Neurology 40*:513–7.

Serban et al, (1990) "Rapid Detection Creuzfeldt–Jakob Disease and Scrapie Prion Proteins," *Neurology 40*:110–7.

Stahl et al., (1993) "Structural Studies of the Scrapie Prion Protein Using Mass Spectrometry and Amino Acid Sequencing," *Biochemistry 32*: 1990–2001.

Taraboulos et al., (1992) "Regional Mapping of Prion Proteins in Brain," *Proc. Natl. Acad. Sci. USA 89*:7620–7624.

Wilesmith and Wells, (1991) "Bovine Spongiform Encephalopathy," *Curr. Topics Microbiol. Immunol. 172* 21–38.

Wilesmith, "Bovine Spongiform Encephalopathy," *Methods in Molecular Medicines: Prion Disease*, pp. 155–73.

Williamson, et al., (1996) "Circumventing tolerance to generate autologous monoclonal antibodies to the prion protein," *Proc. Natl. Acad. Sci. USA 93*: 7279–82.

Schmerr, Mary Jo, et al., "Improvements in a Competition Assay to Detect Scrapie Prion Protein by Capillary Electrophoresis", *Journal of Chromatography B* (1996) 681:29–35.

Yokoyama, Takashi, et al., "Immunoreactivity of Specific Epitopes of PrP $^{Sc}$ is Enhanced by Pretreatment in a Hydrated Autoclave", *Clinical and Diagnostic Laboratroy Immunology* (1996) 3(4):470–471.

ASSAY FOR DISEASE RELATED CONFORMATION OF A PROTEIN

BACKGROUND OF THE INVENTION

This invention relates generally to immunoassays. More particularly the invention relates to an assay which allows for detection of a disease related conformational form of a protein (such as PrP$^{Sc}$) which may have very low antibody binding affinity.

FIELD OF THE INVENTION

Prions are infectious pathogens that cause invariably fatal prion diseases (spongiform encephalopathies) of the central nervous system in humans and animals. Prions differ significantly from bacteria, viruses and viroids. The dominating hypothesis is that no nucleic acid is necessary to allow for the infectivity of a prion protein to proceed.

A major step in the study of prions and the diseases they cause was the discovery and purification of a protein designated prion protein [Bolton, McKinley et al. (1982) Science 218: 1309–1311; Prusiner, Bolton et al. (1982) Biochemistry 21: 6942–6950; McKinley, Bolton et al. (1983) Cell 35: 57–62]. Complete prion protein-encoding genes have since been cloned, sequenced and expressed in transgenic animals. PrP$^C$ is encoded by a single-copy host gene [Basler, Oesch et al. (1986) Cell 46: 417–428] and when PrP$^C$ is expressed it is generally found on the outer surface of neurons. Many lines of evidence indicate that prion diseases results from the transformation of the normal form of prion protein (PrP$^C$) into the abnormal form (PrP$^{Sc}$). There is no detectable difference in the amino acid sequence of the two forms. However, PrP$^{Sc}$ when compared with PrP$^C$ has a conformation with higher β-sheet and lower α-helix content [Pan, Baldwin et al. (1993) Proc Natl Acad Sci USA 90: 10962–10966; Safar, Roller et al. (1993) J Biol Chem 268: 20276–20284]. The presence of the abnormal PrP$^{Sc}$ form in the brains of infected humans or animals is the only disease-specific diagnostic marker of prion diseases.

PrP$^{Sc}$ plays a key role in both transmission and pathogenesis of prion diseases (spongiform encephalopathies) and it is a critical factor in neuronal degeneration [Prusiner (1997) The Molecular and Genetic Basis of Neurological Disease, 2nd Edition : 103–143]. The most common prion diseases in animals are scrapie of sheep and goats and bovine spongiform encephalopathy (BSE) of cattle [Wilesmith and Wells (1991) Curr Top Microbiol Immunol 172: 21–38]. Four prion diseases of humans have been identified: (1) kuru, (2) Creutzfeldt-Jakob Disease (CJD), (3) Gerstmann-Streussler-Sheinker Disease (GSS), and (4) fatal familial insomnia (FFI) [Gajdusek (1977) Science 197: 943–960; Medori, Tritschler et al. (1992) N Engl J Med 326: 444–449]. Initially, the presentation of the inherited human prion diseases posed a conundrum which has since been explained by the cellular genetic origin of PrP.

Most CJD cases are sporadic, but about 10–15% are inherited as autosomal dominant disorders that are caused by mutations in the human PrP gene [Hsiao and Prusiner (1990) Neurology 40: 1820–1827; Goldfarb, Petersen et al. (1992) Science 258: 806–808; Kitamoto and Tateishi (1994) Philos Trans R Soc Lond B 343: 391–398]. However, the human prion diseases are also infectious; the first recognized example being kuru which is believed to spread in New Guinea highlands by ritualistic cannibalism. Another example of human-to-human transmission are cases of iatrogenic CJD, caused by human growth hormone derived from cadaveric pituitaries as well as dura mater grafts [Brown, Preece et al. (1992) Lancet 340: 24–27]. A newly perceived threat of human infection arises in the recent cases of variant CJD with the possible transmission of prions from BSE-infected cows. The seriousness of the health risk resulting from the lack of a direct prion assays in different body fluids, tissue samples or human- and animal-derived pharmaceuticals is exemplified below.

More than 75 young adults who were previously treated with (HGH) human growth hormone derived from human pituitaries have developed CJD [Koch, Berg et al. (1985) N Engl J Med 313: 731–733; Buchanan, Preece et al. (1991) Br Med J 302: 824–828; Fradkin, Schonberger et al. (1991) JAMA 265: 880–884; Brown, Preece et al. (1992) Lancet 340: 24–27]. Fortunately, recombinant HGH is now used, although the seemingly remote possibility has been raised that increased expression of wild-type PrP$^C$ stimulated by high HGH might induce prion disease [Lasmezas, Deslys et al. (1993) Biochem Biophys Res Commun 196: 1163–1169]. The conclusion that the HGH prepared from pituitaries was contaminated with prions, is supported by the transmission of prion disease to a monkey 66 month after inoculation with a suspect lot of HGH [Gibbs, Asher et al. (1993) N Engl J Med 328: 358–359]. Because of the long incubation times associated with prion diseases it will not be possible to determine the full extent of iatrogenic CJD in thousand of people treated with HGH worldwide for decades. Iatrogenic CJD also appears to have developed in four infertile women treated with contaminated human pituitary-derived gonadotropin hormone [Cochius, Mack et al. (1990) Aust N Z J Med 20: 592–593; Cochius, Hyman et al. (1992) J Neurol Neurosurg Psychiatry 55: 1094–1095; Healy and Evans (1993) Br J Med 307: 517–518] as well as at least 11 patients receiving dura mater grafts [Thadani, Penar et al. (1988) J Neurosurg 69: 766–769; Nisbet, MacDonaldson et al. (1989) J Am Med Assoc 261: 1118; Willison, Gale et al. (1991) J Neurol Neurosurg Psychiatry 54: 940; Brown, Preece et al. (1992) Lancet 340: 24–27]. These cases of iatrogenic CJD underscore the need to screen pharmaceuticals that might possibly be contaminated with prions.

Recently, two physicians in France were charged with involuntary manslaughter of a child who had been treated with growth hormones extracted from corpses. The child developed Creutzfeldt-Jakob Disease (see New Scientist, Jul. 31, 1993, page 4). According to the Pasteur Institute, since 1989 there have been 24 reported cases of CJD in young people who were treated with human growth hormone between 1983 and mid-1985. Fifteen of these children have died. It appears that hundreds of children in France have been treated with growth hormone extracted from dead bodies that were at risk for developing CJD (see New Scientist, Nov. 20, 1993, page 10).

Another major concern is the epidemic of BSE in Great Britain and additional cases in some other countries of European Community [Wilesmith (1996) Methods in Molecular Medicine: Prion Diseases : 155–173]. The epidemic spread in the early 80s was probably due to the recycling of prion-infected animals in the rendering process and the feeding of cattle with prion-contaminated protein supplement. The enormous economic cost of eradication of BSE, if ever completely possible [Anderson, Donnelly et al. (1996) Nature 382: 779–788], is now outweighed by the discovery of new variant CJD in young people in Great Britain which was probably transmitted by consumption of BSE-contaminated beef [Collinge, Beck et al. (1996) Lancet 348: 56; Collinge, Sidle et al. (1996) Nature 383: 685–690; Will, Ironside et al. (1996) Lancet 347: 921–925]. Because of the long incubation time of CJD, it is too early to estimate the true extent of threat to the general population in Great Britain and the rest of the Europe from the available epidemiology. The BSE epidemic in cows, the "new variant" CJD and all the cases of iatrogenic CJD in young people underscore the need for screening food sources and pharmaceuticals that might possibly be contaminated with prions.

The most sensitive method today to detect and measure prions is bioassay in transgenic animals overexpressing the cellular prion protein $PrP^C$. The current prion titrations are performed in two steps: (1) the sample material is first injected into susceptible experimental animals to amplify prions and $PrP^{Sc}$ protein to detectable levels; (2) the clinically symptomatic animals are euthanized and the disease is verified by detecting disease-specific $PrP^{Sc}$ and pathology. Since the discovery of protease resistance of $PrP^{Sc}$ more than 15 years ago, the $PrP^{Sc}$ detection is exclusively based on protease treatment of brain samples with proteinase K; the residual C-terminal protease-resistant fragment PrP 27–30 is then detected in denatured form by polyclonal or monoclonal antibodies recognizing prion protein on Western blots. More recent modifications of the same principle are semiquantitative dot blots or qualitative histoblots [Serban, Taraboulos et al. (1990) Neurology 40: 110–117; Taraboulos, Jendroska et al. (1992) Proc Natl Acad Sci USA 89: 7620–7624].

Despite the dramatic shortening of incubation time of human prions in transgenic mice overexpressing chimeric or human PrP genes, in some cases to less than 120 days, the potential for broad and high flow-through application of such prion bioassays is still limited. One possibility further shortening the assay time is to increase the sensitivity of $PrP^{Sc}$ detection. This would shorten the necessary observation time, increase the flow-through and as a result, make assays less expensive and broadly applicable.

Sufficiently sensitive and specific direct assay for infectious $PrP^{Sc}$ in biological samples could potentially abolish the need for animal inoculations completely. Unfortunately, such does not appear to be possible with current $PrP^{Sc}$ assays—it is estimated that the current sensitivity limit of proteinase-K and Western blot-based $PrP^{Sc}$ detection is in a range of 1 $\mu$g/ml which corresponds to $10^4$–$10^5$ prion infectious units. Additionally, the specificity of the traditional proteinase-K-based assays for $PrP^{Sc}$ is in question in light of recent findings of only relative or no proteinase-K resistance of undoubtedly infectious prion preparations [Hsiao, Groth et al. (1994) Proc Natl Acad Sci USA 91: 9126–9130] Telling, et al. (1996) Genes & Dev. In a view of the above points, there is clearly a need for a specific, high flow-through, and cost-effective assay for testing sample materials for the presence of infectious form of prion protein, $PrP^{Sc}$, which is believed to be the cause of prion diseases, such as BSE, CJD and scrapie. The presented invention offers such an assay.

SUMMARY OF THE INVENTION

The assay of the invention is useful in assaying samples which contain proteins which proteins are present in at least two conformations e.g., a native non-disease conformation and a disease conformation. At present, it is quite difficult to generate antibodies which bind to the tightly folded conformation that many proteins assume in their disease form e.g., $PrP^{Sc}$. The present invention utilizes antibodies which do not bind or have a relatively low degree of affinity for the tightly configured disease-conformation of the protein. The assay is carried out by providing a sample which is divided into a first portion and a second portion. The first portion is bound to a first solid support and then contacted with a labeled antibody which binds to the non-disease form of the protein with a higher degree of affinity (e.g., 4 to 30 fold higher affinity) than the antibody binds to the disease form. The second portion of the sample is treated in a manner which causes the tightly bound disease form of the protein present in the sample (if any) to assume a more relaxed conformation which has a higher binding affinity to the labeled antibody. After treatment the second portion is also bound to the surface of a solid support. Thereafter, the second portion is contacted with the same type of labeled antibodies which were used on the first portion. The level of the antibody binding to protein in the first portion is then determined as is the level of antibody binding to a protein in the second treated portion. The difference between the two is determined and if it is found that the level of binding to the proteins in the second portion is significantly higher than that of the first portion it is possible to deduce that the original sample contained proteins in the tightly bound disease related conformation. Further, by use of formulae provided herein it is possible to determine the amount of the disease related conformation of the protein present in the original sample per unit of volume.

To demonstrate the basic concept behind the present invention it is necessary to include a starting sample which is divided into at least two portions. The first portion is contacted with labeled antibodies without treating the proteins and the second portion is treated with labeled antibodies after the proteins have been treated in a manner which causes any proteins in the disease conformation to assume a conformation which has a higher degree of binding affinity for the antibodies. The readings are compared (i.e., one subtracted from the other) and the presence of proteins in the disease related conformation are deduced based on the difference between the two readings. However, it is possible to utilize the basic concept behind the present invention without obtaining two readings for each assay. This can be done by establishing a standard based on carrying out the assay on a statistically significant number of closely related samples. After the standard has been established one will know the level of antibody binding which should be observed when the sample does not contain any proteins in the disease related conformation. Using the standard, one then treats a sample to be tested so as to convert any proteins in the disease related conformation to a different conformation which has a much higher degree of binding affinity for the label antibodies. The measurement obtained is then compared with the standard. If the difference between the standard and the measurement obtained is outside of a given range it can be deduced that the original sample included proteins in the disease related conformation. A third embodiment of the invention can utilize either of the embodiments disclosed above along with the formulae provided herein in order to calculate (quantitatively) the number of proteins in the disease related conformation present within the original sample.

The different embodiments of the assay of the invention described above are all "direct" types of immunoassays—meaning that the sample is directly assayed with the labeled antibody either with or without treatment to change the conformation of any disease related conformation proteins present in the sample. An "indirect" assay may also be used. For example, it may be desireable to enhance the number of disease related proteins in the sample (if any) by the use of a transgenic mouse and thereby enhance any signal obtained. To carry out these embodiments of the invention, the sample is first used to inoculate a transgenic mouse which has had its genome modified so that it will develop symptoms of disease when inoculated with proteins in the disease related conformation. After the mice are inoculated a sufficient period of time is allowed to pass (e.g., 30 days) after which the transgenic animal is sacrificed and a sample such as homogenized brain tissue from a mouse is used in the direct assay described above. The present invention enhances the ability of transgenic mice to detect prions by shortening the period of time which must pass until a determination can be made as to whether the original sample included proteins in the disease related conformation. It would also be possible to apply epitope tagged PrP as disclosed in pending U.S. patent application Ser. No. 08/660,626, filed Jun. 6, 1996 to affinity purify the PrP$^{Sc}$ from the brain of a Tg mouse and thereafter apply the assay of the present invention. Without the present invention the mouse is inoculated and the tester must wait until the inoculated mouse actually demonstrates symptoms of the disease. Depending on the mouse this can take several months or even years.

The assay methodology of the present invention can be applied to assaying any type of sample when the sample is suspected of containing a protein which protein occurs in at least two conformations. The protein must occur in one conformation which binds to known antibodies or antibodies which can be generated. The second conformation must be sufficiently different from the first conformation in terms of its binding affinity so that the two conformations can be distinguished by using antibodies which have a much higher degree of affinity for the first conformation than for the second conformation. In its conceptually simplest form the invention works best when a known labeled antibody binds to a non-disease form of a protein with a high degree of affinity and does not bind or binds with an extremely low degree of affinity to the same protein when it is present in its disease related conformation. However, in reality a given protein may have more than two conformations. The protein may have more than one non-disease conformation and more than one disease related conformation, Telling, et al., Science (1996). The invention is still useful when multiple conformations of non-disease and disease forms of the protein exist -provided that (1) at least one non-disease conformation differs from at least one disease conformation in terms of its binding affinity; and (2) it is possible to treat the disease related conformation of the protein so as to substantially enhance its binding affinity.

As indicated above the assay of the invention can be used to assay any type of sample for any type of protein provided the protein includes a non-disease and a disease related conformation. However, the invention was particularly developed to assay samples for the presence PrP proteins and determine whether the sample included a PrP protein in its disease conformation, i.e., included PrP$^{Sc}$. Accordingly, much of the following disclosure is directed to using the immunoassay of the present invention to detect the presence of a PrP$^{Sc}$ in a sample—it being understood that the same general concepts are applicable to detecting disease related conformations of a wide range of different types of proteins.

The present method of PrP$^{Sc}$ detection was developed by labeling selected purified IgG with Europium. Antibodies used have a high binding affinity for PrP$^C$ (non-disease conformation) which comprises an α-helical configuration. The antibodies have a low binding affinity for PrP$^{Sc}$ (disease conformation) which comprises a β-sheet configuration. The IgG may be obtained from common monoclonal, polyclonal, or recombinant antibodies, typically recognizing the sequence 90–145 or 222–231 of conformationally unfolded prion protein. Different conformations of recombinant prion protein were chemically crosslinked to polystyrene plates through a glutaraldehyde activation step. The relative affinities of the Eu-labeled IgG with α-helical, β-sheet, and random coil conformation of recombinant Syrian hamster prion protein corresponding to sequence 90-231 were determined by time-resolved, dissociation-enhanced fluorescence in a 96-well polystyrene plate format. The calibration of the method revealed a large increase in antibody reactivity in the transition from β-sheet conformational state to denatured state, and only a small increase in the transformation from its native α-helical to the treated relaxed, or denatured state. Thus, the original conformational state of prion protein can be assigned by the differential assay in native and treated states. The amount of antibody-specific binding over that expected for α-helical conformation of $PrP^{C}$ is a measure of the presence of β-sheet conformation which is essential for pathogenicity and infectivity of $PrP^{Sc}$.

A primary object of the invention is to provide an immunoassay which is applicable to assaying samples containing proteins which samples are suspected of containing a protein which occurs within a native non-disease conformation and a disease related conformation.

An advantage of the present invention is that the immunoassay can quickly and accurately determine the presence of proteins in the disease related conformation even thought the antibody used in the assay does not bind or has a very low degree of binding affinity for the protein in the disease related conformation.

A feature of the invention is that the signal obtained can be enhanced by the use of transgenic mice.

Another advantage of the present invention is that the results obtained can be applied to the formulae provided herein in order to determine the number of proteins in the disease related conformation present in the original sample.

A specific object is to provide a diagnostic assay for determining the presence of infectious prion protein in variable sample materials obtained or derived from human, primate, monkey, pig, bovine, sheep, deer, elk, cat, dog, and chicken tissues and/or body fluids.

Another object is to provide a rapid assay for native infectious prion protein in the brains of transgenic and non-transgenic animals injected with sample material potentially containing prions.

Another object is to shorten the time needed to carry out prion bioassays in transgenic and non-transgenic animals to 30 days or less.

Another object is to provide a method to evaluate prion decontamination procedures by assaying the level of denaturation of pathogenic prion protein after such treatments.

Another object is to provide a rapid method for screening different compounds to evaluate their potential for treating diseases associated with disease conformations of different proteins such as by screening compounds for their stabilizing effect on different protein conformations or their destabilizing impact on the pathogenic conformation of a protein.

Another object is to provide a rapid method for screening different pharmaceutical compounds with potential for prion disease treatment such as by screening compounds for their stabilizing effect on α-helical conformation of a normal isoform of the $PcP^{C}$ protein or their destabilizing impact on the β-sheet conformation of the pathogenic isoform of the $PrP^{Sc}$ protein.

Still another object is to provide a rapid method to screen the impact of different spontaneous and designer mutations in the prion protein gene on conformation, stability and resulting infectivity of such prion protein gene products—de novo prions.

The specific advantage is that invented process can be used as an assay for the presence of the disease form of any protein such as prions in products such as pharmaceuticals (derived from natural sources), food, cosmetics or any materials which might contain prions and thereby provide further assurances as to the safety of these products.

Another advantage is that the assay may detect pathogenic forms of prion protein in a mixture with denatured noninfectious forms of the same protein or in a mixture with a normal isoform of prion protein—for example, detect the presence of $PrP^{Sc}$ when present in an amount of less than 5% in a composition.

Another advantage is that in the invented process there is no need for an antibody directly able to recognize infectious conformation of prion protein, or to use a proteinase K step to eliminate the signal of normal (non-disease) isoforms of the protein such as $PrP^C$.

An important feature of the assay is the rapid, cost effective and high flow-through design which can be designed with the capacity to screen 96 samples per day per 96 well plate.

These and other objects, advantages, and features of the invented process will become apparent to those skilled in the art upon reading the details of the assay method, antibody development and testing, and transgenic mouse as more fully described below with reference to the attached figures.

DETAILED DESCRIPTION OF THE PREFERRED EMBODIMENTS

Figure 1:
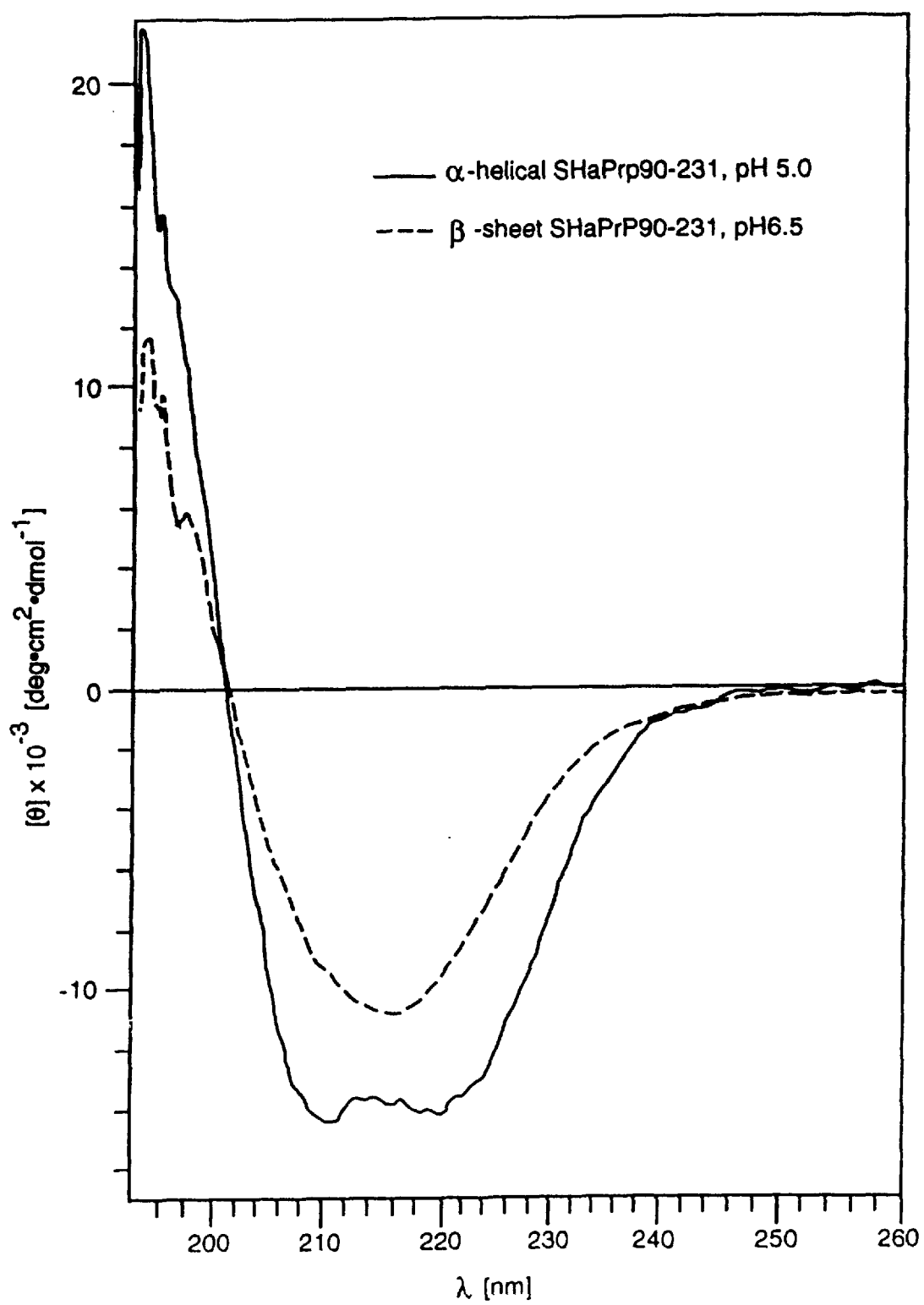
FIG. 1 is a spectrograph of the conformation of recombinant SHaPrP90-231 as determined by circular dichroism (CD) spectroscopy showing the two major bands with minima at 208 and 222 nm indicate α-helical conformation; single negative band with minimum at 217 nm is characteristic of predominantly β-sheet conformation.

Before the present assays and methods are disclosed and described, it is to be understood that this invention is not limited to particular antibodies, proteins, labels, assays or method as such may, of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Definitions

The terms "protein" as used herein is intended to encompass any amino acid sequence and include modified sequences such as glycoproteins. The term includes naturally occurring proteins and peptides as well as those which are synthetically synthesized. As used in connection with the present invention the term "protein" is specifically intended to cover naturally occurring proteins which occur in at least two different conformations wherein both conformations have the same or substantially the same amino acid sequence but have different three dimensional structures. The two conformations of the protein include at least one conformation which is not related to a disease state and at least one conformation which is related to a disease state. A specific and preferred example of a protein as used in connection with this disclosure is a PrP protein which includes the non-disease form referred to as the PrP$^C$ form and the disease related form referred as the PrP$^{Sc}$.

The terms "treating", "treatment" and the like are used interchangeably here to describe a process whereby a sample or portion thereof and specifically proteins in the sample are physically and/or chemically manipulated so that proteins in the sample in a disease related conformation are caused to changed to a different conformation with a higher antibody binding affinity. Treated proteins are also referred to as denatured proteins or proteins in a relaxed conformation which conformation increases the antibody binding affinity of the protein. Treating includes subjecting the sample to heat, pressure and/or chemicals. In a preferred embodiment samples containing PrP$^{Sc}$ (which is a disease conformation comprising β-sheet structural configurations) are treated so that the protein assumes a different conformation (e.g., comprising an α-helical configuration and/or a random coil configuration) having four times or more greater antibody binding affinity.

The terms "PrP protein", "PrP" and like are used interchangeably herein and shall mean both the infectious particle form PrP$^{Sc}$ known to cause diseases (spongiform encephalopathies) in humans and animals and the noninfectious form PrP$^C$ which, under appropriate conditions is converted to the infectious PrP$^{Sc}$ form.

The terms "prion", "prion protein" and "PrP$^{Sc}$ protein" and the like we used interchangeably herein to refer to the infectious PrP$^{Sc}$ form of PrP and is a contraction of the words "protein" and "infection" and particles are comprised largely if not exclusively of PrP$^{Sc}$ molecules encoded by a PrP gene. Prions are distinct from bacteria, viruses and viroids. Known prions infect animals to cause scrapie, a transmissible, degenerative disease of the nervous system of sheep and goats, as well as bovine spongiform encephalopathy (BSE), or mad cow disease, and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a prion protein. Some commonly known PrP sequences are described in Gabriel et al., Proc. atl. Acad. Sci. USA 89, 9097–9101 (1992) which is incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a PrP$^C$ (non-disease) or PrP$^{Sc}$ (disease) form.

The terms "standardized prion preparation", "prion preparation", "preparation" and the like are used interchangeably herein to describe a composition obtained from the brain tissue of mammals which exhibits signs of prion disease: the mammal either (1) include a transgene as described herein; (2) have and ablated endogenous prion protein gene; (3) have a high number of prion protein gene from a genetically diverse species; or (4) are hybrids with an ablated endogenous prion protein gene and a prion protein gene from a genetically diverse species. The mammals from which standardized prion preparations are obtained exhibit clinical signs of CNS dysfunction as a result of inoculation with prions and/or due to developing the disease of their genetically modified make up, e.g., high copy number of prion protein genes.

The term "artificial PrP gene" is used to encompass the term "chimeric PrP gene" as well as other recombinantly constructed genes which, when included in the genome of a host animal (e.g. a mouse, will render the mammal susceptible to infection from prions which naturally only infect a genetically diverse test animal, e.g. human, bovine or ovine. In general, an artificial gene will include the codon sequence of the PrP gene of the mammal being genetically altered with one or more (but not all, and generally less than 40) codons of the natural sequence being replaced with a different codon preferably a corresponding codon of a genetically diverse mammal (such as a human). The genetically altered mammal being used to assay samples for prions only affect the genetically diverse mammal. Examples of artificial genes are mouse PrP genes encoding the sequence for human, cows and sheep and replacing mouse codons at the same relative positions, with the provision that not all the mouse codons are replaced with differing human, cow or sheep codons. Artificial PrP genes can include not only codons of genetically diverse animals but may include codons and codon sequences not associated with any native PrP gene but which, when inserted into an animal render the animal susceptible to infection with prions which would normally only infect an genetically diverse animal.

The terms "chimeric gene", "chimeric PrP gene", "chimeric prion protein gene" and the like are used interchangeably herein to refer to an artificially constructed gene containing the codons of a host animal such as a mouse with one or more of the codons replaced with corresponding codons from a genetically diverse test animal such as a human, cow or sheep. In one specific example, the chimeric gene is comprised of the starting and terminating sequence (i.g., N- and C-terminal codons) of PrP gene of a mammal of host species (e.g. a mouse) and also containing a nucleotide sequence of a corresponding portion of a PrP gene of a test mammal of a second species (e.g. a human). When a chimeric gene is inserted into the genome of the host species, it will render the mammal susceptible to infection with prions which normally infect only mammals of the second species. The preferred chimeric gene disclosed herein is MHu2M which contains the starting and terminating sequence of a mouse PrP gene and a non-terminal sequence region which is replaced with a corresponding human sequence differing from a mouse PrP gene at nine residues.

The term "genetic material related to prions" is intended to cover any genetic material which affects the ability of an animal to become infected with prions. Thus the term encompasses any "PrP gene", "artificial PrP gene", "chimeric PrP gene" or "ablated PrP gene" which terms are defined herein as well as modification of such which effect the ability of an animal to become infected with prions. Standardized prion preparations are produced using animals which all have substantially the same genetic material related to prions so that all of the animals will become infected with the same type of prions and will exhibit signs of infection at approximately the same time.

The term "host animal" and "host mammal" are used to describe animals which will have their genome genetically and artificially manipulated so as to include genetic material which is not naturally present within the animal. For example, host animals include mice, hamsters and rats which have their PrP gene ablated i.e., rendered inoperative. The host is inoculated with prion proteins to generate antibodies. The cells producing the antibodies are a source of genetic material for making a phage library. Other host animals may have a natural (PrP) gene, or one which is altered by the insertion of an artificial gene or by the insertion of a native PrP gene of a genetically diverse test animal.

The term "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog or chicken, and one may wish to determine whether a particular sample includes prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster.

The term "ablated PrP protein gene", "disrupted PrP gene", and the like are used interchangeably herein to mean an endogenous PrP gene which has been altered (e.g., add and/or remove nucleotides) in a manner so as to render the gene inoperative. Examples of non-functional PrP genes and methods of making such are disclosed in Bueler, H., et al "Normal development of mice lacing the neuronal cell-surface PrP protein" Nature 356, 577–582 (1992) and Weissmann (WO 93/10227). The methodology for ablating a gene is taught in Capecchi, Cell 51:503–512 (1987) all of which are incorporated herein by reference. Preferably both alleles of the genes are disrupted as represented by $PrP^{0/0}$ or $Prnp^{0/0}$.

The terms "hybrid animal"; "transgenic hybrid animal" and the like are used interchangeably herein to mean an animal obtained by the cross-breeding of a first animal having an ablated endogenous prion protein gene with a second animal which includes either (1) a chimeric gene or artificial PrP gene or (2) a PrP gene from a genetically diverse animal. For example a hybrid mouse is obtained by cross-breeding a mouse containing an ablated mouse gene with a mouse containing (1) human PrP genes (which may be present in high copy numbers) or (2) chimeric genes. The term hybrid includes any offspring of a hybrid including inbred offspring of two hybrids provided the resulting offspring is susceptible to infection with prions with normal infect only a genetically diverse species. A hybrid animal can be inoculated with prions and serve as a source of cells for the creation of hybridomas to make monoclonal antibodies of the invention.

The terms "susceptible to infection" and "susceptible to infection by prions" and the like are used interchangeably herein to describe a transgenic or hybrid test animal which develops a disease if inoculated with prions which would normally only infect a genetically diverse test animal. The terms are used to describe a transgenic or hybrid animal such as a transgenic mouse Tg(MHu2M) which, without the chimeric PrP gene, would not come infected with a human prion but with the chimeric gene is susceptible to infection with human prions.

The term "antibody" stands for an immunoglobulin protein which is capable of binding an antigen. Antibody as used herein is meant to include the entire antibody as well as any antibody fragments (e.g. F(ab', Fab, Fv) capable of binding the epitope, antigen or antigenic fragment of interest. Preferred antibodies for assays of the invention are immunoreactive or immunospecific for and therefore specifically and selectively bind to a PrP protein. Antibodies which are immunoreactive and immunospecific for both native $PrP^C$ and treated $PrP^{Sc}$ but not native $PrP^{Sc}$ are preferred. Antibodies for PrP are preferably immunospecific—e.g., not substantially cross-reactive with related materials. The term "antibody" encompasses all types of antibodies, e.g. polyclonal, monoclonal, and those produced by the phage display methodology. Particularly preferred antibodies of the invention are antibodies which have a relatively high degree of affinity for both native $PrP^C$ and treated $PrP^{Sc}$ but a relatively low degree of or substantially no binding affinity for $PrP^{Sc}$. More specifically, antibodies of the invention preferably have four times or more, more preferably fifteen times or more, and still more preferably 30 times or more binding affinity for both native $PrP^C$ and denatured $PrP^{Sc}$ as compared with the binding affinity for native $PrP^{Sc}$.

"Purified antibody" refers to that which is sufficiently free of other proteins, carbohydrates, and lipids with which it is naturally associated. Such an antibody "preferentially binds" to a treated or denatured $PrP^{Sc}$ protein (or an antigenic fragment thereof), and does not substantially recognize or bind to other antigenetically unrelated molecules. A purified antibody of the invention is preferably immunoreactive with and immunospecific for a specific species and more preferably immunospecific for native $PcP^C$ and for treated or denatured forms of $PrP^C$ and $PrP^{Sc}$ but not for native or untreated $PrP^{Sc}$.

"Antigenic fragment" of a protein (e.g., a PrP protein) is meant a portion of such a protein which is capable of binding an antibody.

By "binds specifically" is meant high avidity and/or high affinity binding of an antibody to a specific polypeptide e.g., epitope of a protein, e.g., a $PrP^C$ protein. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to epitope fragments of a protein such as $PrP^{Sc}$ so that by adjusting binding conditions the antibody binds almost exclusively to an epitope site or fragments of a desired protein such as an epitope fragment exposed by treatment of $PrP^{Sc}$ and not exposed on native untreated $PrP^{Sc}$.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)). Europium is a particularly preferred label.

Abbreviations used herein include:

CNS for central nervous system;

BSE for bovine spongiform encephalopathy;

CJD for Creutzfeldt-Jacob Disease;

FFI for fatal familial insomnia;

GSS for Gerstamnn-Strassler-Scheinker Disease;

Hu for human;

HuPrP for human prion protein;

Mo for mouse;

MoPrP for mouse prion protein;

SHa for a Syrian hamster;

SHaPrP for a Syrian hamster prion protein;

Tg for transgenic;

Tg(SHaPrP) for a transgenic mouse containing the PrP gene of a Syrian hamster;

Tg(HuPrP) for transgenic mice containing the complete human PrP gene;

Tg(ShePrP) for transgenic mice containing the complete sheep PrP gene;

Tg(BovPrP) for transgenic mice containing the complete cow PrP gene;

$PrP^{Sc}$ for the scrapie isoform of the prion protein;

$PrP^C$ for the cellular contained common, normal isoform of the prion protein;

$MoPrP^{Sc}$ for the scrapie isoform of the mouse prion protein;

MHu2M for a chimeric mouse/human PrP gene wherein a region of the mouse PrP gene is replaced by a corresponding human sequence which differs from mouse PrP at 9 codons;

Tg(MHu2M) mice are transgenic mice of the invention which include the chimeric MHu2M gene;

$MHu2MPrP^{Sc}$ for the scrapie isoform of the chimeric human/mouse PrP gene;

$PrP^{CJD}$ for the CJD isoform of a PrP protein;

$Prnp^{0/0}$ for ablation of both alleles of an endogenous prion protein gene, e.g., the MoPrP gene;

$Tg(SHaPrP^{+/0})81/Prnp^{0/0}$ for a particular line (81) of transgenic mice expressing SHaPrP, +/0 indicates heterozygous;

$Tg(HuPrP)/Prnp^{0/0}$ for a hybrid mouse obtained by crossing a mouse with a human prion protein gene (HuPrP with a mouse with both alleles of the endogenous prion protein gene disrupted;

$Tg (MHu2M)/Prnp^{0/0}$ for a hybrid mouse obtained by crossing a mouse with a chimeric prion protein gene (MHu2M) with a mouse with both alleles of the endogenous prion protein gene disrupted.

FVB for a standard inbred strain of mice often used in the production of transgenic mice since eggs of FVB mice are relatively large and tolerate microinjection of exogenous DNA relatively well.

GENERAL ASPECTS OF THE INVENTION

The assay method comprises providing a sample suspected of containing a protein which assumes a first conformation and a second disease related conformation. The sample is divided into a first portion and a second portion. The first portion is preferably bound to the surface of the solid support and thereafter brought into contact with a labeled antibody. The antibody is of a type which binds to the protein in its first configuration with a higher (four times or more) degree of affinity than it binds to the protein in its second disease related conformation. The second portion of the sample is then treated in a manner which causes any protein in the second, disease related conformation to assume a different conformation which conformation has a higher degree of affinity (four times or more higher) for the labeled antibody as compared with the affinity for the protein in the second disease related conformation. The treated second portion is then, preferably, bound to the surface of the solid support. The treated protein bound to the support is then contacted with a labeled antibody under conditions which allow the antibody to bind to proteins in the first configuration or proteins in the assumed different configuration.

Figure 3:
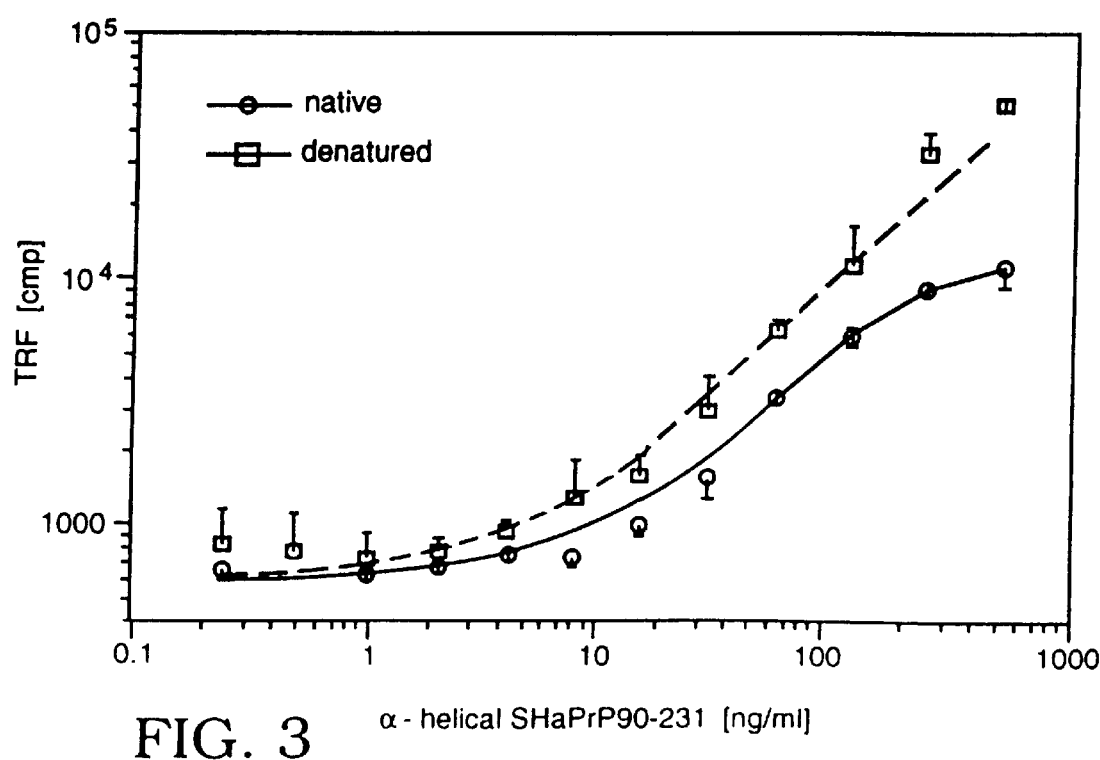
FIG. 3 is a graph showing the calibration of a direct assay with recombinant SHaPrP90-231 in α-helical conformation, in the presence of 5% $PrP^{0/0}$ mouse brain homogenate wherein the data points and bars represent average±SEM obtained from four independent measurements.
Figure 4:
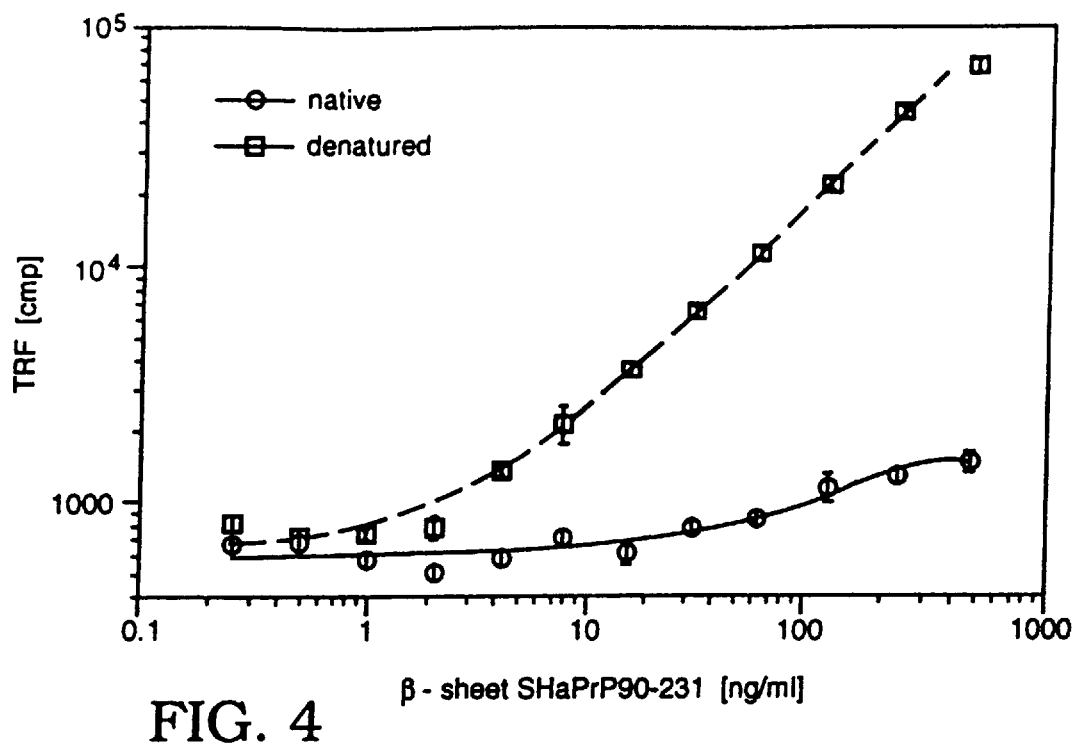
FIG. 4 is a graph showing the calibration of a direct assay with recombinant SHaPrP90-231 in β-sheet conformation, in the presence of 5% $PrP^{0/0}$ mouse brainhomogenate wherein the data points and bars represent average±SEM obtained from four independent measurements.
Figure 5:
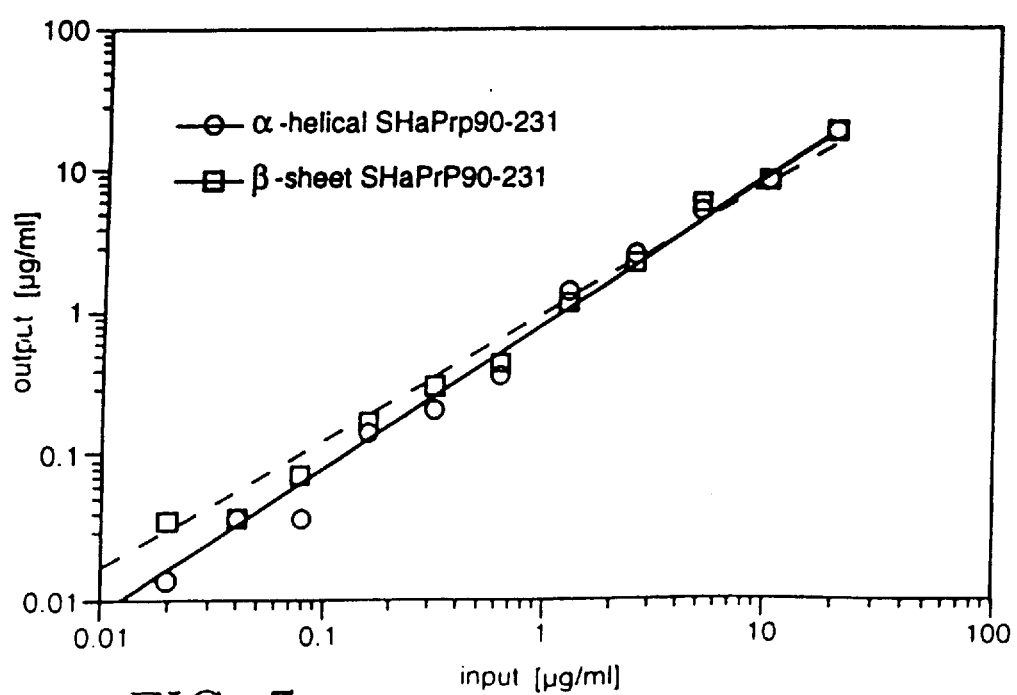
FIG. 5 is a graph showing the input-output validation of a direct assay for both α-helical and β-sheet forms of SHaPrP90-231 in the presence of 5% $PrP^{0/0}$ mouse brain homogenate wherein the amount of the protein on the x axis was determined by amino acid analysis and the amount of the protein on the y axis is calculated from the assay.

After the labeled antibodies have been provided with sufficient time, temperature and chemical conditions to bind to the appropriate proteins present in the respective portions the level of binding of the labeled antibody to protein in each portion is determined. The level of binding is then compared. For example, the level of binding of labeled antibody to a protein in the first portion is subtracted from the level of binding of antibody to a protein in the second portion. The difference between the two reflects the amount of protein present in the original sample which was in the second, disease related conformation—after adjusting for differences caused (if any) by increasing the binding affinity of protein in the first portion. More specifically, with some proteins there may be some differences due to the effect of the treatment on the proteins which are in the native non-diseased conformation. This differential should be accounted for in drawing conclusions with respect to whether the original sample included proteins in the second, disease related conformation. Accounting for this effect is relatively straightforward as shown within FIGS. 3 and 4. In FIG. 3 there is shown a comparison of antibody binding to an untreated sample which contains only native protein in its non-disease configuration with the same native protein after treatment. As shown within FIG. 3 there is some difference between the results obtained with the treated protein showing a stronger signal in that the treatment increased the binding affinity of the protein. However, FIG. 4 shows the same results when the original sample included proteins which were in the second, disease related conformation. The native proteins which are not treated provide a very weak signal. However, the treated proteins provide a very strong signal. The large differential between the treated and the untreated samples is a clear indication that the original sample included proteins with the second, disease related conformation in that these proteins do not bind to antibodies or bind to antibodies with a very low degree of binding affinity. However, after treatment these proteins bind to the antibodies as well or nearly as well or better than the proteins in the non-disease conformation which were treated.

The assay can be used to test for the presence of the disease conformation of a given protein within any type of sample. Some of the most typical samples to be tested include pharmaceuticals which include components which are derived from living mammals or use materials derived from living mammals and their processing. It would also be desireable to test organs for transplantation and food items such as beef which was suspected of containing infectious prions. However, the invention could be used for testing for the presence of the disease conformation of one or more types of proteins such as infectious $PrP^{Sc}$ in pharmaceuticals, cosmetics, biopsy or autopsy tissue, brain, spinal cord, peripheral nerve, muscle, cerebrospinal fluid, blood and blood components, lymph nodes, and in animal or human-derived cultures infected or potentially infected by disease forms of proteins such as prions.

As indicated above, "treating" can include exposing the proteins to any physical and/or chemical means which causes the protein which is originally present in a tightened, disease related conformation to assume a more relaxed conformation which has a higher degree of binding affinity for antibodies. In general, the treatment or denaturing as it is sometimes referred to herein involves subjecting the protein to some means which causes epitopes on the protein which were not previously exposed to become exposed so that an antibody can bind to the newly exposed epitope. The methods of treatment which can be used include: (1) physical, such as hydrostatic pressure or temperature, (2) chemical, such as acidic or alkaline pH, chaotropic salts, or denaturing detergents, and (3) combinations of above.

The method of chemical or affinity coupling of PrP protein to the plastic support are generally described in available literature and may vary. The antibodies used in the diagnostic assay are polyclonal, monoclonal or recombinant Fab and need to be species specific with preferential binding to the native $PrP^C$ or denatured form of $PrP^{Sc}$ with preferably at least 4-fold lower reactivity with infectious $PrP^{Sc}$, assuming the same amount of the antigen.

Using the Assay to Detect Prions

The core of the invention consists of a two step process to diagnose prion disease by quantitatively measuring native infectious form of $PrP^{Sc}$ protein in sample material or in the brains of susceptible animals inoculated with such material. The sample is divided into two aliquots. The first aliquot is crosslinked to the solid plastic support in native conformation through a chemical activation step under the nondenaturing conditions, i.e., no treating. The second portion of the sample is first treated and then crosslinked to the plastic support. Both portions of the sample material react in situ with the labeled antibodies that preferentially recognize native $PrP^C$ or treated $PrP^{Sc}$ of the given animal species. The amount of the antibody bound to treated or native conformations of PrP protein is recorded by the signal of the IgG label. The excess of the signal obtained with the denatured sample over that expected from an increase in the signal obtained with the native α-helical conformation of $PrP^{C}$ is the measure of the amount of infectious β-sheet structured $PrP^{Sc}$ in the original sample. The formula developed for calculation of $PrP^{Sc}$ content is shown in herein and exemplified in Example 11.

The diagnosis of prion disease is established by three procedures: (1) measurement of treated sample alone and by detecting the increase in the total PrP amount in the examined sample above the background levels of $PrP^{C}$ obtained from normal controls; (2) calculation of the ratio between denatured versus native signal for a given antibodies—for example values higher than 2.2 for Europium-labeled 3F4 IgG indicates presence of $PrP^{Sc}$; (3) evaluation of the excess of the denatured sample signal over that expected from increase in the signal for α-helical conformation of $PrP^{C}$ as a measure of the amount of infectious β-sheet structured $PrP^{Sc}$ in the original sample.

In a scrapie infected Syrian hamster brain, the concentration of $PrP^{Sc}$ is 5–10 times higher than $PrP^{C}$ when the animals become ill. At this time, the prion titer in their brains is $10^7$–$10^8$ $ID_{50}$ units/ml. of 10% homogenate. The highly quantitative system that we have developed allows us to subtract the $PrP^{C}$ signal. The subtraction can be readily carried out when the concentration of $PrP^{Sc}$ is greater than $PrP^{C}$. However, the subtraction becomes difficult when the concentration of $PrP^{Sc}$ is much less than $PrP^{C}$.

To address the foregoing problem, the present assay utilizes the principle of affinity between different conformations of antigen and antibody. To measure the concentration of $PrP^{Sc}$ when it is much less than $PrP^{C}$, the detection system has to have extreme sensitivity and a linear range of at least $10^4$. The assay described herein can readily detect $PrP^{Sc}$ at a concentration of (approximately) 50 pg/ml using Europium labeled IgG. Assuming $10^5$–$10^6$ $PrP^{Sc}$ molecules per $ID_{50}$ unit the present assay can readily detect $5\times10^2$–$5\times10^3$ $ID_{50}$ units per ml.

The assay can detect prpsc in mixtures (by direct method) where the concentration of $PrP^{Sc}$ is less than 1% of the concentration of PrPC. Additional sensitivity can be achieved by immunoprecipitation, using a sandwich format for a solid state assay, differfential centrifugation with detergent extraction to remove $PrP^{C}$, the indirect transgenic animal method or combinations of these methods. A conservative estimate is that such procedures should allow measurement of between 5 and 50 $ID_{50}$ units per ml or less conservatively to measure between 0.1 and 0.01 $ID_{50}$ units per ml. Such measurements would provide a rapid, "positive" means of establishing biological sterility which is the "absence" of infectivity.

Method of Drug Identification

The assays described above which can identify the presence of a disease related conformation of a protein can be applied to identifying compounds which could then be used as drugs in treating or preventing diseases associated with the disease conformation of the protein. For example, compositions which are known to include disease related conformations of a protein can be used to inoculate a transgenic mouse of the type described above. The inoculated mouse can then be treated with a compound which is believed to prevent the infection. After providing for a sufficient period of time for incubation, the mouse brain is extracted and tested using the assay described above to determine if the treatment compound was effective in preventing infection. The methodology could also be applied to situations where the infection had already taken place in order to determine if a particular compound could stabilize the infection i.e., prevent further formation of the disease conformation of the protein.

The assay of the present invention can be used in combination with the methodology disclosed within earlier filed U.S. patent application Ser. No. 08/556,823, filed Nov. 2, 1995. This application discloses compounds which can be brought into contact with proteins in a non-disease conformation in order to convert those compounds to a disease conformation. The methodology is useful in that it allows one to screen compounds for their ability to prevent the formation of the disease related conformation of the protein. The assay of the present invention makes it possible to accurately measure the effect of any test compound on preventing the formation of the disease related conformation.

Based on the above it can be seen that the invention includes a method of screening compounds which affect the conformational shape of any protein such as a PrP protein which has a first non-disease related conformation (e.g., PrP$^C$) and a second disease related conformation (e.g., PrP$^{Sc}$). The method involves first providing a sample having the protein present in the first, non-disease conformation. The sample is then brought into contact with a test compound which is being screened for its therapeutic utility. After adding the test compound the sample is then brought into contact with a compound or group of compounds which induce the protein in the first, non-disease conformation to convert to the second, disease-conformation. After allowing for a sufficient period of time the sample is assayed using the present invention. The assay of the present invention will make it possible to accurately determine how the test compound affected the conversion of the protein from the non-disease conformation to the disease conformation. It will be apparent to those skilled in the art reading this disclosure that the test compound can be added at different points in time relative to the addition of the compound which affects the conformational change. Thereby, the methodology can be used to determine the ability of a test compound to stabilize further changes from the non-disease conformation to the disease conformation and/or determine the ability of th test compound to prevent the initiation of any conversion from the non-disease conformation to the disease conformation. Although U.S. patent application Ser. No. 08/556,823, filed Nov. 2, 1995 (incorporated herein by reference) discloses a means for converting a non-disease conformation to a disease conformation other means for obtaining the same result will become apparent to those skilled in the art upon reading the present application and reviewing the state of the art in connection with such. Accordingly, the present invention is intended to encompass any physical, chemical or biological means which would be utilized to convert a protein within a first, non-disease conformation to a second, disease conformation and applying the assay described here. Further, the present invention is intended to encompass therapeutic compunds which are obtained as a result of carrying out the screening method of the invention, i.e., compounds produced by the method of the invention.

Antibodies

The antibodies detecting treated forms of PrP$^{Sc}$ protein and PrP$^C$ protein may be generated by immunizing rabbits or mice with α-helical conformations of recombinant PrP, native PrP$^C$ from animal brains, synthetic peptides in α-helical or random coil conformations, or against denatured PrP$^{Sc}$ or PrP 27–30. Only antibodies with affinity at least 4 fold higher for PrP$^C$ (or denatured conformation of PrP$^{Sc}$ of the same species) as compared to their affinity for PrP$^{Sc}$ should be selected. The method of antibody generation, purification, labeling and detection may vary.

The IgG or Fab's may be purified from different sources by affinity HPLC using protein A column and Size exclusion HPLC. The purified antibodies may be labeled with Europium and detected by time resolved fluorescence. The antibody binding to different conformations of PrP protein may be measured by time-resolved, dissociation-enhanced fluorescence. However, the system of detection of PrP-bound IgG on solid support in situ or in solution may vary. Further, it is possible to use direct or indirect immunological methods including direct radiolabeles, fluorescence, luminescence, avidin-biotin amplification, or enzyme-linked assays with color or luminescent substrates.

Quantitative Calculations

Using the methodology described above it is possible to calculate the difference between the amount of signal obtained from a sample which has not been treated and the signal obtained with a sample which has been treated. This difference represents (after adjusting for the effect of treatment on the non-disease conformation) the amount of protein in disease conformation present in the original sample. After obtaining the difference the formula put forth below can be used to calculate the amount of protein in the disease conformation present in the original sample per unit of volume.

a) $F_n = F_{n\alpha} + F_{n\beta} \rightarrow F_{n-\alpha} = F_n - F_{n\beta}$, $F_{n\beta}$~background b) $F_d = F_{d\alpha} + F_{d\beta}$ $$\Delta F_{n \rightarrow d} = \Delta F_{\alpha n \rightarrow d} + \Delta F_{\beta n \rightarrow d}$$
$$\Delta F_{\beta n \rightarrow d} = \Delta F_d - \Delta F_{\alpha n \rightarrow d}$$
$$[PrP_\beta] \sim \Delta F_{\beta n \rightarrow d} = \Delta F_d - (F_n * f_{\alpha n \cdot d})$$

The definition of each of the above variables is provided below.

F—fluorescence signal (note that any detectable signal could be used);

$F_n$—fluorescence signal of native conformation;

$F_{n\alpha}$ and $F_{n\beta}$—fluorescence signals of native α-helical and β-sheet conformations, respectively;

$F_d$—fluorescence signal of PrP in the treated or denatured state;

$F_{d\alpha}$ and $F_{d\beta}$—are the signals of denatured α-helical of β-sheet states of PrP;

$\Delta F_{n \rightarrow d}$—increase of the fluorescence signal in the transition from native to denatured state;

$\Delta F_{\alpha n \rightarrow d}$—increase in the fluorescence signal of α-helical conformation in the transition from native to denatured state;

$\Delta F_{\beta n \rightarrow d}$—increase in the signal of β-sheet conformation in the transition from native to denatured state;

$f_{\alpha n \rightarrow d}$—correlation factor for the transition from native to denatured state of α-helical PrP;

$[PrP_\beta]$—concentration of prion protein in β-sheet conformation.

The formula put forth above along with the defined variables can be used to calculate the concentration of the disease related conformation of a variety of different proteins. However, the above definitions have been provided specifically with respect to PrP proteins which proteins include at least one non-disease conformation (PrP$^C$) which includes an α-helical configuration and at least one disease related conformation (PrP$^{Sc}$) which includes a β-sheet configuration. The formulae are used to calculate the concentration of the disease related conformation of the protein present in the sample. Per the specific formulae and definitions provided above the formulae are used to calculate the concentration of prion proteins which include the β-sheet configuration (see Example 11).

The signal used in calculating the above formula is a fluorescence signal. However, any detectable signal can be used. The total signal is represented by $F_n$ which is a combination of the signal received from the disease and the non-disease related conformations. This is a signal which would be calculated from portion No. 1 which is not treated per the assay described above. The variable $F_d$ is the signal which is obtained by treating portion No. 2 of the sample. This signal is a combination of the signal received from treated protein in the non-disease conformation plus treated protein in the disease conformation.

It has been recognized that there is a difference in signal obtained by treating a sample which includes no disease related conformation of the protein. The difference should be accounted for to obtain an accurate reading. The difference in signal obtained between the native sample and the treated sample is, of course, a combination of the difference in signal obtained by treating the disease related conformation and the non-disease conformation. The increase in the signal obtained by treating the disease conformation, i.e., the difference between the signal of the untreated disease conformation and the signal received from the treated disease conformation can be calculated by subtracting the signal received from treating the entire sample from the signal received from calculating the increase in signal obtained from the untreated non-disease conformation and the treated non-disease conformation. Using these equations it is possible to produce the final equation which provides the concentration of protein in the disease conformation present in the original sample (see Example 11).

Diseases Associated with Insoluble Proteins

Much of the disclosure and the specific examples provided herein relate to the use of the assay in connection with determining the presence of PrP$^{Sc}$ in the sample. However, as indicated above, the assay of the invention can be applied to determining the presence of any protein which assumes two different conformational shapes, one of which is associated with the disease. The following is a non-limiting list of diseases with associated insoluble proteins which assume two or more different conformations.

| Disease | Insoluble Proteins |
|---|---|
| Alzheimer's Disease | APP, Aβ peptide, α1-antichymotrypsin, tan, non-Aβ component |
| Prion diseases, Creutzfeld Jakob disease, scrapie and bovine spongeform encephalopathy | PrP$^{Sc}$ |
| ALS | SOD and neurofilament |
| Pick's disease | Pick body |
| Parkinson's disease | Lewy body |
| Diabetes Type 1 | Amylin |
| Multiple myeloma-- plasma cell dyscrasias | IgGL-chain |
| Familial amyloidotic polyneuropathy | Transthyretin |
| Medullary carcinoma of thyroid | Procalcitonin |
| Chronic renal failure | β$_2$--microglobulin |
| Congestive heart failure | Atrial natriuretic factor |
| Senile cardiac and systemic amyloidosis | Transthyretin |
| Chronic inflammation | Serum amyloid A |
| Atherosclerosis | ApoA1 |
| Familial amyloidosis | Gelsolin |

It should be noted that the insoluble proteins listed above each include a number of variance or mutations which are intended to be encompassed by the present. Known pathogenic mutations and polymorphisms in the PrP gene related to prion diseases are given below and the sequences of human, sheep and bovine are given in U.S. Pat. No. 5,565,1865, issued Oct. 15, 1996.

MUTATION TABLE

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro—Leu | | | |
| Codon 105 Pro—Leu | | | |
| Codon 117 Ala—Val | | | |
| Codon 145 Stop | | | |
| Codon 178 Asp—Asn | | | |
| Codon 180 Val—Ile | | | |
| Codon 198 Phe—Ser | | | |
| Codon 200 Glu—Lys | | | |
| Codon 210 Val—Ile | | | |
| Codon 217 Asn—Arg | | | |
| Codon 232 Met—Ala | | | |

It should also be noted that such proteins have two different 3-dimensional conformations with the same amino acid sequence. One conformation is associated with disease characteristics and is generally insoluble whereas the other conformation is not associated with disease characteristics and is soluble.

Specifics of a PrP Protein

The major component of purified infectious prions is the core which is designated PrP 27-30. It is this proteinase K resistant core of the larger native protein PrP$^{Sc}$ which signifies the disease causing form and distinguishes this form from the ubiquitous cellular protein PrP$^C$. PrP$^{Sc}$ is found only in scrapie infected cells whereas PrP$^C$ is present in both infected and uninfected cells implicating PrP$^{Sc}$ as the major, if nor sole, component of infectious prion particles.

Since both PrP$^C$ and PrP$^{Sc}$ are encoded by the same single copy gene, great effort has been directed toward unraveling the mechanism by which PrP$^{Sc}$ is derived from PrP$^C$. Central to this goal has been the characterization of physical and chemical differences between these two molecules. Properties distinguishing PrP$^{Sc}$ from PrP$^C$ include low solubility [Meyer, McKinley et al. (1986) Proc Natl Acad Sci USA 83: 2310–2314], poor antigenicity [Kascsak, Rubenstein et al. (1987) J Virol 61: 3688–3693; Serban, Taraboulos et al. (1990) Neurology 40: 110–117], protease resistance [Oesch, Westaway et al. (1985) Cell 40: 735–746], and polymerization of PrP 27–30 into rod shaped aggregates which are very similar, on the ultrastructural and histochemical levels, to the PrP amyloid plaques seen in scrapie diseased brains [Prusiner, McKinley et al. (1983) Cell 35: 349–358]. To date, attempts to identify any post-transitional chemical modifications in PrP$^C$ that lead to its conversion to PrP$^{Sc}$ have proven fruitless [Stahl, Baldwin et al. (1993) Biochemistry 32: 1991–2002]. Consequently, it has been proposed that PrP$^C$ and PrP$^{Sc}$ are in fact conformational isomers of the same molecule.

Conformational description of PrP using conventional techniques has been hindered by problems of solubility and the difficulty in producing sufficient quantities of pure protein. However, PrP$^C$ and PrP$^{Sc}$ are conformationally distinct. Theoretical calculations based upon the amino acid sequences of PrP proteins from several species have predicted four putative helical motifs in the molecule. Experimental spectroscopic data would indicate that in PrP$^C$ these regions adopt α-helical arrangements, with virtually no β-sheet [Pan, Baldwin et al. (1993) Proc Natl Acad Sci USA 90: 10962–10966; Safar, Roller et al. (1995) Research Advances in Alzheimer's Disease and Related Disorders : 775–781]. In dramatic contrast, in the same study it was found that PrP$^{Sc}$ and PrP 27-30 posses significant β-sheet content, which is typical of amyloid proteins [Pan, Baldwin et al. (1993) Proc Natl Acad Sci USA 90: 10962–10966; Safar, Roller et al. (1993) J Biol Chem 268: 20276–20284]. Moreover, studies with extended synthetic peptides, corresponding to PrP amino acid residues 90–145, have demonstrated that these truncated molecules may be converted to either α-helical or β-sheet structures by altering their solution conditions. The transition of PrP$^C$ to PrP$^{Sc}$ requires the adoption of β-sheet structure by regions that were previously α-helical. It is believed that the β-sheet structural configuration does not provide exposed epitopes which bind well to antibodies, whereas an α-helical structured configuration does provide exposed epitopes which have a higher affinity for antibodies.

In general, scrapie infection fails to produce an immune response, with host organisms being tolerant to PrP$^{Sc}$ from the same species. Polyclonal anti-PrP antibodies have though been raised in rabbits following immunization with large amounts of formic acid or SDS-denatured SHaPrP 27–30 [Bendheim, Barry et al. (1984) Nature 310: 418–421; Bode, Pocchiari et al. (1985) J Gen Virol 66: 2471–2478; Safar, Ceroni et al. (1990) Neurology 40: 513–517]. Similarly, a handful of anti-PrP monoclonal antibodies against PrP 27-30 have been produced in mice [Barry and Prusiner (1986) J Infect Dis 154: 518–521; Kascsak, Rubenstein et al. (1987) J Virol 61: 3688–3693]. These antibodies were generated against formic acid or SDS-denatured PrP 27-30 and are able to recognize native $PrP^C$ and treated or denatured $PrP^{Sc}$ from both SHa and humans equally well, but do not bind to MoPrP. Not surprisingly, the epitopes of these antibodies were mapped to regions of the sequence containing amino acid differences between SHa- and MoPrP [Rogers, Yehiely et al. (1993) Proc Natl Acad Sci USA 90: 3182–3186].

It is not entirely clear as to why antibodies of the type described in the above cited publications will bind to $PrP^C$ and treated or denatured $PrP^{Sc}$ but not to native $PrP^{Sc}$. Without being bound to any particular theory it is suggested that such may take place because epitopes which are exposed when the protein is in the $PrP^C$ conformation are unexposed or partially hidden in the $PrP^{Sc}$ configuration—where the protein is relatively insoluble and more compactly folded together.

For purposes of the invention an indication that no binding occurs means that the equilibrium or affinity constant $K_a$ is $10^6$ l/mole or less. Further, binding will be recognized as existing when the $K_a$ is at $10^7$ l/mole or greater preferably $10^8$ l/mole or greater. The binding affinity of $10^7$ l/mole or more may be due to (1) a single monoclonal antibody (i.e., large numbers of one kind of antibodies) or (2) a plurality of different monoclonal antibodies (e.g., large numbers of each of five different monoclonal antibodies) or (3) large numbers of polyclonal antibodies. It is also possible to use combinations of (1)–(3). Selected preferred antibodies will bind at least 4-fold more avidly to the treated or denatured $PrP^{Sc}$ forms of the protein when compared with their binding to the native conformation of $PrP^{Sc}$. The four fold differential in binding affinity may be accomplished by using several different antibodies as per (1)–(3) above and as such some of the antibodies in a mixture could have less than a four fold difference.

Antibody/Antigen Binding Forces

The forces which hold an antigen and antibody together are in essence no different from non-specific interactions which occur between any two unrelated proteins i.e., other macromolecules such as human serum albumin and human transferrin. These intermolecular forces may be classified into four general areas which are (1) electrostatic; (2) hydrogen bonding; (3) hydrophobic; and (4) Van der Waals. Electrostatistic forces are due to the attraction between oppositely charged ionic groups on two protein side-chains. The force of attraction (F) is inversively proportional to the square of the distance (d) between the charges. Hydrogen bonding forces are provided by the formation of reversible hydrogen bridges between hydrophilic groups such as —OH, $—NH_2$, and —COOH. These forces are largely dependent upon close positioning of two molecules carrying these groups. Hydrophobic forces operate in the same way that oil droplets in water merge to form a single large drop. Accordingly, non-polar, hydrophobic groups such as the side-chains on valine, leucine and phenylalanine tend to associate in an aqueous environment. Lastly, Van der Waals are forces created between molecules which depend on interaction between the external electron clouds. All the above interaction depend on complementarity between conformation of the antigen and antibody recognition site.

Further information regarding each of the different types of forces can be obtained from "Essential Immunology edited by I. M. Roitti (6th Edition) Blackwell Scientific Publications, 1988. With respect to the present invention useful antibodies exhibit all of these forces. It is by obtaining an accumulation of these forces in larger amounts that it is possible to obtain an antibody which has a high degree of affinity or binding strength to the PrP protein and in particular an antibody which has a high degree of binding strength to the configuration of $PrP^C$ and/or the random coil configuration obtained by treating any β-sheet PrP protein in situ.

Standard Prion Preparation

Standardized prion preparations can be produced in order to test assays of the invention and to calibrate and validate the diagnostic sensitivity, specificity, positive and predictive value. For example, a transgenic mouse containing a human prion protein gene can produce human prions and the brain of such mouse can be used to create a standardized human prion preparation. Further, in order to obtain a standardized preparation a large number (e.g. 100, 1,000, or animals) of essentially identical animals are used. For example, 100 mice all containing a very high copy number of hamster or human PrP genes (with all polymorphisms and mutations) would develop disease and the brain tissue from each could be combined to make a useful standardized prion preparation.

Standardized prion preparations can be produced using any of the modified host mammals described in U.S. U.S. Pat. No. 5,565,186, issued Oct. 15, 1996 and U.S. patent application Ser. No. 08/521,992, filed Aug. 31, 1995, incorporated to disclose transgenic animals and methods of making and using same. For example, standardized prion preparations could be produced using mice, rats, hamsters, or guinea pigs which are genetically modified so that they are susceptible to infection with prions which would generally only infect genetically diverse species such as a human, cow, sheep, or horse and which modified host mammals will develop clinical signs of CNS dysfunction within a period of time of 350 days or less after inoculation with prions. The most preferred host mammal is a mouse in part because they are inexpensive to use and because a greater amount of experience has been obtained with respect to production of transgenic mice than with respect to the production of other types of host animals. Details regarding making standardized prion preparation are described in U.S. Patent application entitled "Method of Detecting Prions in as Sample and Transgenic Animal Used For Same" filed Aug. 31, 1995, Ser. No. 08/521,992 and U.S. patent application Ser. No. 08/692,842, filed Jul. 30, 1996 "Detecting Prions In A Sample And Prion Preparation And Transgenic Animal Used For Same", both of which applications are incorporated herein by reference.

Once an appropriate type of host is chosen, such as a mouse, the next step is to chose the appropriate type of genetic manipulation to be utilized to produce a standardized prion formulation. The next step is to produce large numbers of such animals which are substantially identical in terms of genetic material related to prions. More specifically, each of the mice produced will include an identical chimeric gene present in the genome in substantially the same copy number. The mice should be sufficiently identical genetically in terms of genetic material related to prions that 95% or more of the mice will develop clinical signs of CNS dysfunction within 350 days or less after inoculation and all of the mice will develop such CNS dysfunction at approximately the same time e.g. within ± 30 days of each other.

Once a large group e.g., 50 or more, preferably 500 or more of such mice are produced, the next step is to inoculate the mice with prions which generally only infect a genetically diverse mammal e.g. prions from human, sheep, cow, or horse. The amounts given to different groups of mammals could be varied. After inoculating the mammals with the prions the mammals are observed until the mammals exhibit symptoms of prion infection e.g. clinical signs of CNS dysfunction. After exhibiting the symptoms of prion infection the brain or at least a portion of the brain tissue of each mammals is 30 extracted. The extracted brain tissue is homogenized and provides the standardized prion preparation.

As an alternative to inoculating a group of transgenic mice with prions from genetically diverse animal it is possible to produce mice which spontaneously develop prion related disease. This can be achieved by including extremely high copy numbers of a human PrP gene into the mouse genome. When the copy number is raised to, for example, 100 or more copies, the mouse will spontaneously develop clinical signs of CNS dysfunction and have, within its brain tissue, prions which are capable of infecting humans. The brains of these animals or portions of the brain tissue of these animals can be extracted and homogenized to produce standardized prion preparations.

The standardized prion preparations can be used directly or can be diluted and titered in a manner so as to provide for a variety of different positive controls. Such a diluted composition has to be used in detecting the presence of prions to test the sensitivity of the assays and methods of the invention

EXAMPLES

The following examples are put forth so as to provide those of ordinary skill in the art with a complete disclosure and description of how to make and use chimeric genes, transgenic mammals and assays of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Expression of Recombinant Prion Proteins

For the development and calibration of the diagnostic assays, recombinant Syrian hamster prion proteins of sequence 90-231 were refolded into α-helical or β-sheet conformations as described [Mehlhorn, Groth et al. (1996) Biochemistry 35: 5528–5537]. The PCR (Perkin-Elmer) was used to amplify the DNA corresponding to different portions of the Syrian hamster prion protein in order to ligate it into *E. coli* secretion vectors. Several 5' oligonucleotide primers were synthesized with an Mlu I restriction site within the C-terminal coding sequence of the STII signal peptide [Lee, Moseley et al. (1983) Infect Immun 42: 264–268; Picken, Mazaitis et al. (1983) Infect Immun 42: 269–275] and the initial amino acids of the appropriate PrP sequence. One 3' oligonucleotide primer matching the 3' end of PrP, a stop codon and a Bam HI restriction site was used with each of the 5' oligonucleotides. The PCR amplified products were purified, ligated into the vectors previously digested with MluI/Bam HI and transformed into DH5a. Clones containing the PrP insert were sequenced and transformed into the protease deficient expression strain 27C7 (ATCC# 55244).

Large scale expression was carried out as described previously for other proteins using a different medium [Carter, Kelley et al. (1992) Biotechnology 10: 163–167]; 500 mL of an overnight culture grown in LB medium supplemented with ampicillin was inoculated into 7 L of fermentation medium in an aerated 10 L fermentor (Braun, model E10). Cells were grown at 37 ° C. at a high agitation rate and expression was induced by phosphate starvation. After 4 h, a 50% glucose solution was added at a rate of 1 mL/min; glucose levels were monitored using a glucose dipstick (Diastix, Miles Inc.). A pH of 7.4 was maintained throughout the run by the automated addition of 10% H2SO4 or 24% NH4OH. The final volume was 10 L in which an OD600 of ≧100 was achieved after 36 h. The *E. coli* was harvested by centrifugation at 10,000×g for 30 min and the resulting paste was stored at −20° C.

For purification, 100 g of *E. coli* paste was resuspended in 1 L of 25 mM Tris.HCl, pH 8.0/5 mM EDTA (buffer A). This was centrifuged at 10,000×g for 20 min and the supernatant containing soluble periplasmic proteins was discarded. The pellet was resuspended in 1 L of buffer A, passed through a cell disrupter twice (Microfluidics International, model MF110), and centrifuged at 30,000×g for 1 h, after which the supernatant was discarded and the pellet was washed once in buffer A and centrifuged again at 30,000×g for 1 h. At this stage the pellet could be stored at −20° C. prior to further separation. It was subsequently solubilized in 8M GdnHCl/25 mM Tris-HCl, pH 8.0/100 mM DTT (buffer B) and centrifuged at 14,000×g for 20 min to remove the remaining insoluble matter. Aliquots of 6 mL of the supernatant containing ~200 mg total protein were separated by size exclusion chromatography (SEC) using a 26 mm×60 cm HiLoad Superdex 200 column (Pharmacia), eluting with 6M GdnHCl/12.5 mM Tris-HCl, pH 8.0/SmM DTT/1 mM EDTA (buffer C) at a flow rate of 2 mL/min. Fractions enriched for the recombinant prion protein as identified by SDS-PAGE were pooled and further purified by reversed phase high performance liquid chromatography (RP-HPLC) employing a 25 mm×25 cm C-4 column (Vydac); Buffer 1: H20/0.1% TFA, Buffer 2: acetonitrile/0.09% TFA, flow rate 5 mL/min. The recombinant protein rPrP was found in fractions containing 40% acetonitrile. If the SEC eluate was stored at 4° C. for several days prior to RP-HPLC, the recombinant protein was eluted in earlier fractions containing only 35% acetonitrile.

Samples of the reduced protein and the refolded oxidized form were concentrated using a Centricon (Amicon) with a molecular weight cut-off of 10,000 Da. The buffer for the reduced protein was 10 mM MES, pH 6.5 whereas the oxidized form was concentrated in the refolding buffer described above. The conformations of refolded oxidized and reduced forms of SHaPrP90-231 protein were determined by circular dichroism (CD) spectroscopy (FIG. 1).

Example 2

Purification of Hamster PrP$^C$ from Normal and PrP$^{Sc}$ from Scrapie Infected Hamster Brains Both proteins produced per Example 1 were used as a standards for the prion assay and to establish the sensitivity and linearity range of the diagnostic method. The purified Syrian hamster brain PrP$^C$ was used for the calibration of prion protein detection and correlated with results obtained on recombinant SHaPrP90-231 in α-helical, β-sheet, and denatured conformations. The PrP$^C$ protein was purified as described with some minor modifications [Pan, Stahl et al. (1992) Protein Sci 1:

1343–1352; Pan, Baldwin et al. (1993) Proc Natl Acad Sci USA 90: 10962–10966]. Protein content was determined by amino acid analysis. The purity of PrP$^C$ protein, as demonstrated on SDS PAGE followed by silver staining and Western, was ≧95%.

Standard Syrian hamster PrP$^{Sc}$ was purified from a standard pool of scrapie strain Sc237 infected hamster brains as described with only minor modifications [Turk, Teplow et al. (1988) Eur J Biochem 176: 21–30]. The infectivity of this standard, as determined by an incubation time assay on Syrian hamsters after intracerebral inoculation, was $10^{7.3}$ ID$_{50}$/ml and specific infectivity $10^{8.2}$ ID$_{50}$/mg of PP$^{Sc}$ protein. However, the specific infectivity may vary from lot to lot ± $10^{0.5}$ ID$_{50}$/mg. The protein content was determined by BCA assay using Bovine serum albumin as a standard. The preparation was considered homogeneous with one major band on SDS PAGE after silver staining and Western Blots.

Example 3

Selection, Labeling and Detection Method of Antibodies Used in the Assay

The protocols and methods of antibody production and characterization are in general described elsewhere [Harlow and Lane (1988) : 726]. The data described in this and following examples were generated with immunoaffinity purified polyclonal antibody N12 and P3 [Safar, Ceroni et al. (1990) Neurology 40: 513–517; Rogers, Serban et al. (1991) J Immunol 147: 3568–3574], made against synthetic peptides corresponding sequence 90–145 (N12) and 222–231 (P3) of Syrian Hamster PrP [Barry, Vincent et al. (1988) J Immunol 140: 1188–1193];

JS2 against denatured Syrian Hamster PrP 27–30 [Safar, Ceroni et al. (1990) Neurology 40: 513–517]. The development and characteristics of monoclonal antibody 3F4 used in the assay are described elsewhere [Kascsak, Rubenstein et al. (1987) J Virol 61: 3688–3693] and are described in U.S. Pat. No. 4,806,627 all of which are incorporated by reference to disclose and describe antibodies which can be used with the invention and methods of making those and related antibodies. The recombinant Fab recognizing denatured forms of prion protein were developed most recently [Williamson, Peretz et al. (1996) Proc Natl Acad Sci USA 93: 7279–7282].

SHaPrP90-231 in α-helical, β-sheet and random coil conformations were covalently attached to the glutaraldehyde activated polystyrene plates and incubated with serially diluted primary antibody. The amount of IgG reacting with each conformation of SHaPrP90-231 was determined either directly with Eu-labeled 3F4 IgG, or indirectly with Europium labeled anti-rabbit or anti mouse antibody, according to usual protocols and the total signal was measured by time-resolved, dissociation-enhanced fluorescence. For the assay development were selected antibodies with the signal ratio of denatured versus β-sheet conformation of SHaPrP90-231 equal or higher than 4.

Example 4

Competitive and Direct Assay Format

Purified recombinant SHaPrP90-231, refolded into -α-helical or β-sheet conformation, was diluted into 5% (w/v) brain homogenate obtained from PrP$^{0/0}$ mouse and containing no prion protein. The brain homogenate was made by three 30 sec bursts in PowerGen homogenizer equipped with plastic disposable probe in TBS, pH 7.4 containing protease inhibitors cocktail (1 mM PMSF, 2 μg/ml of Aprotinin, and 2 μg/ml of Leupeptin) and spun at 5° C. for 5 min at 500 G in desktop centrifuge. The resulting supernatant was diluted 1:1 in TBS with final 4% (w/v) Sarcosyl and homogenized again by three 30 sec bursts in a PowerGen homogenizer. Next, the homogenate was spiked with different dilutions of recombinant SHaPrP90-231 in α-helical or β-sheet conformations.

Figure 2:
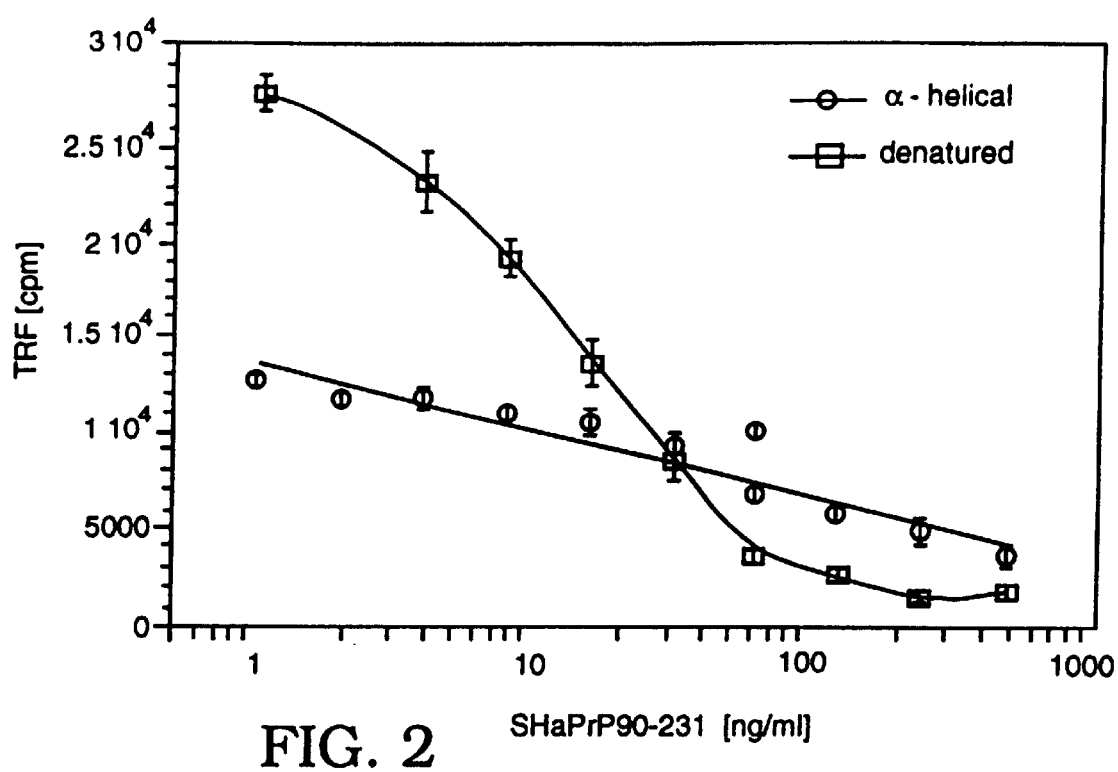
FIG. 2 is a graph showing the results of competitive assay of recombinant SHaPrP90-231 in α-helical and denatured conformations in the presence of 5% $PrP^{0/0}$ mouse brain homogenate wherein the difference in slope and crossover points obtained with Europium-labeled 3F4 IgG indicate that each conformations has both a different affinity and number of binding sites and further wherein the data points and bars represent average±SEM obtained from four independent measurements.

In a typical competitive assay, the analyte PrP in different conformations is preincubated with Europium labeled 3F4 IgG and then transferred to the polystyrene plate coated with recombinant SHaPrP90-231 in SDS-denatured state. The results for analyte SHaPrP90-231 in α-helical and denatured state (FIG. 2) indicate marked difference in both available binding sites and affinity of Europium-labeled 3F4 IgG with different conformations of prion protein.

In direct assay, each sample of dilution curve was divided into two aliquots: (1) untreated and designated native; (2) mixed with final 4M Gdn HCl and heated for 5 min at 100° C. and designated denatured. Both samples were diluted 20-fold by H$_2$O and aliquots loaded on polystyrene plate activated with glutaraldehyde. The plates, incubated overnight at 5° C., were blocked with TBS, pH 7.8, containing 0.5% BSA (w/v) and 6% Sorbitol (w/v). In the next step, they were washed three time with TBS, pH 7.8 containing 0.05% (v/v) of Tween 20 and incubated with Europium-labeled antibodies listed above. The plates were developed after an additional 7 washing steps in enhancement solution provided by the Europium label supplier (Wallac Inc, Turku, Finland) and signal counted on DELFIA 1234 Fluorometer (Wallac Inc, Turku, Finland).

Example 5

Differential Test for Various Conformations of SHaPrP90-231

The parameters obtained from direct assay with Eu-labeled 3F4 IgG were plotted as a function of the concentration. The results obtained with SHaPrP90-231 in α-helical conformation (FIG. 3) indicate relatively small difference between signal of α-helical and denatured protein. The sensitivity limit for denatured PrP in the presence of 5% brain homogenate is $\leq 1$ ng/ml and linearity range over 3 orders of magnitude. In the experiments with the β-sheet form of SHaPrP90-231 (FIG. 4), Eu-labeled 3F4 IgG bind strongly to a denatured form of the protein. In contrast, the reactivity with the native β-sheet form of the protein only marginally exceeded the background even at high protein concentrations. When the results are expressed as a ratio of the fluorescence of denatured versus native states of the prion protein (FIGS. 3 and 4), the ratio for α-helical conformation is 1–1.8 and for recombinant SHaPrP90-231 in β-sheet conformation is 5–50.

Figure 6:
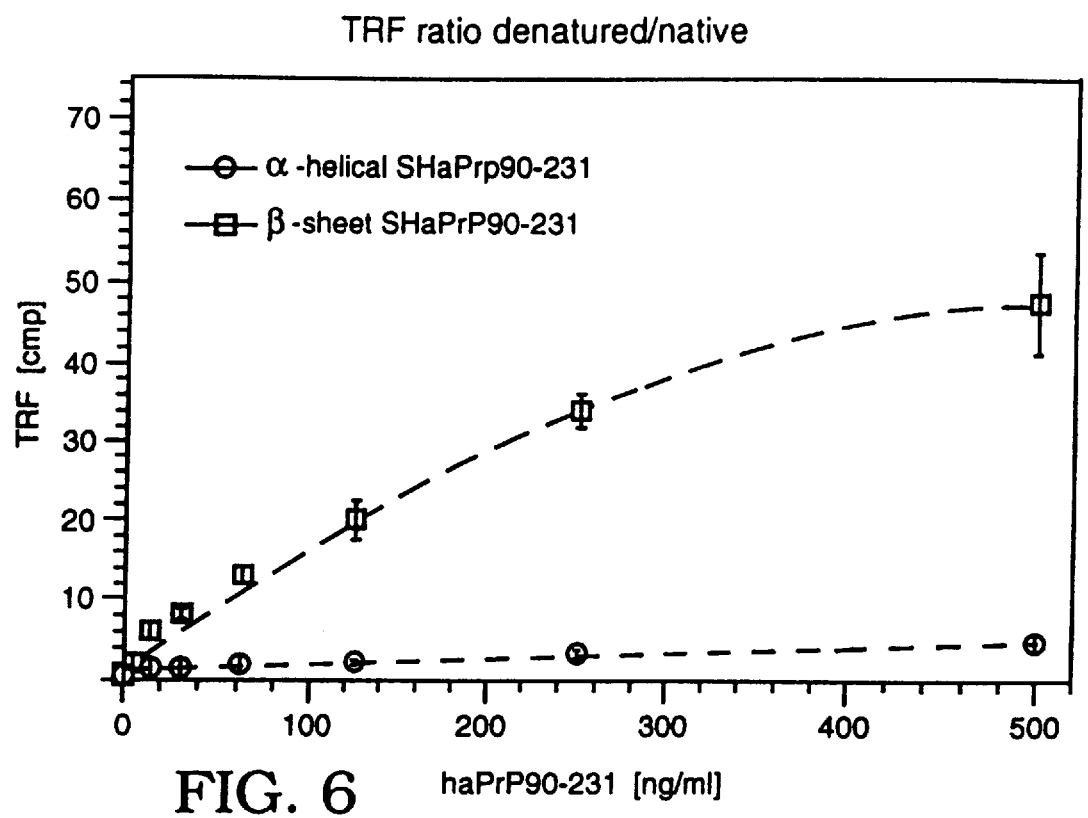
FIG. 6 is a graph showing the ratio between the signals of treated (denatured) and native SHaPrP90-231 in α-helical and β-sheet conformations, developed with Eu-labeled 3F4 IgG wherein the data points and bars represent average±SEM obtained from four independent measurements.
Figure 7:
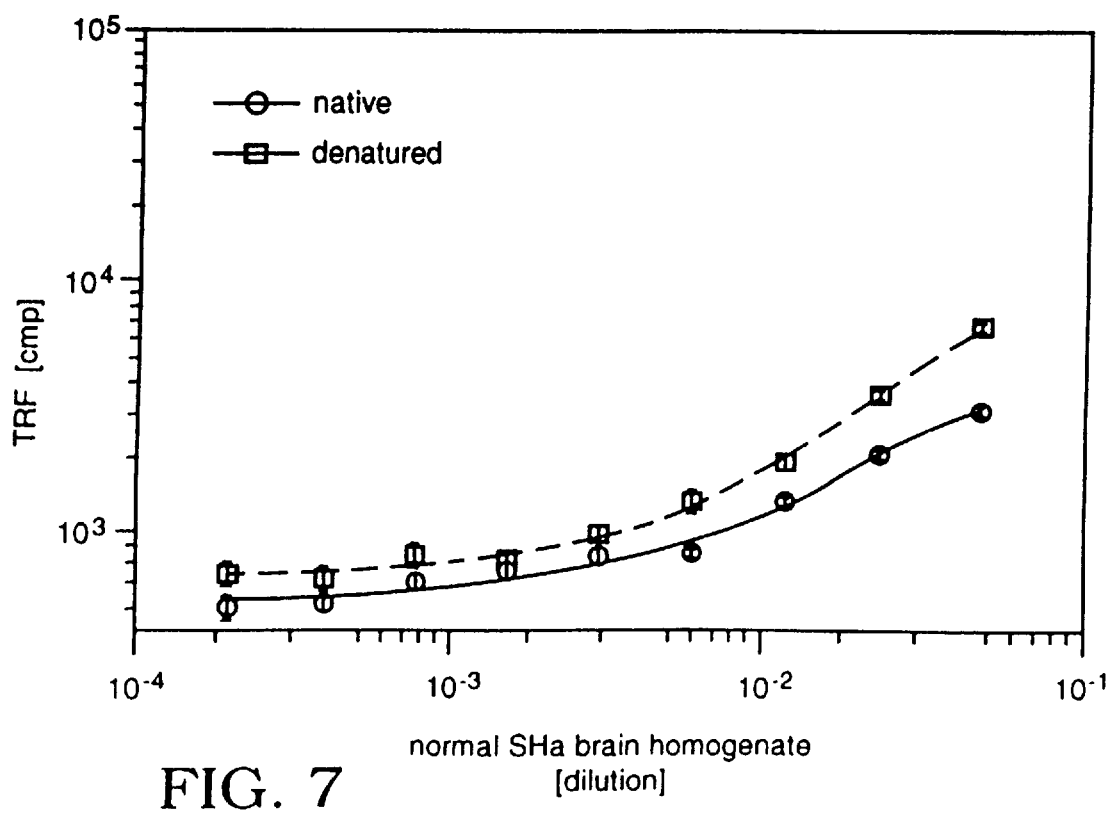
FIG. 7 is a graph showing the results of a direct assay for $PrP^C$ protein in normal hamster brain homogenate wherein the data points and bars represent average±SEM obtained from four independent measurements.
Figure 8:
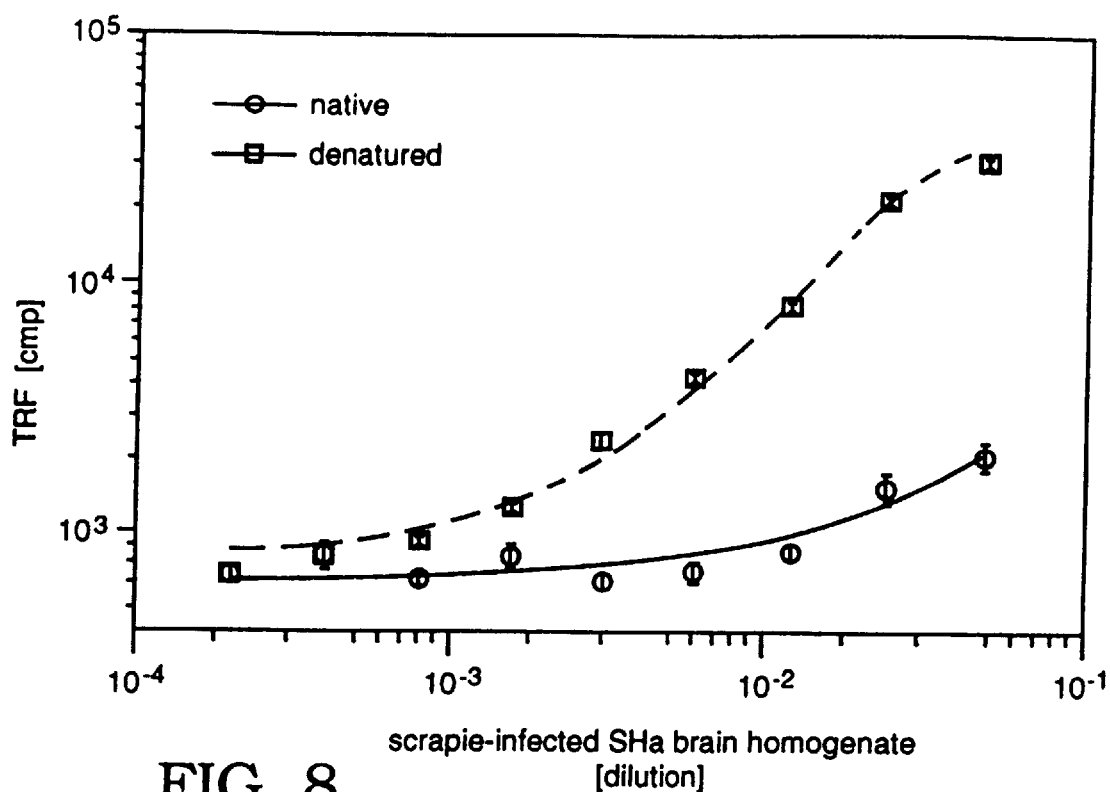
FIG. 8 is a graph showing the results of a direct assay for $PrP^{C+Sc}$ in scrapie infected hamster brain homogenate wherein the data points and bars represent average±SEM obtained from four independent measurements.
Figure 9:
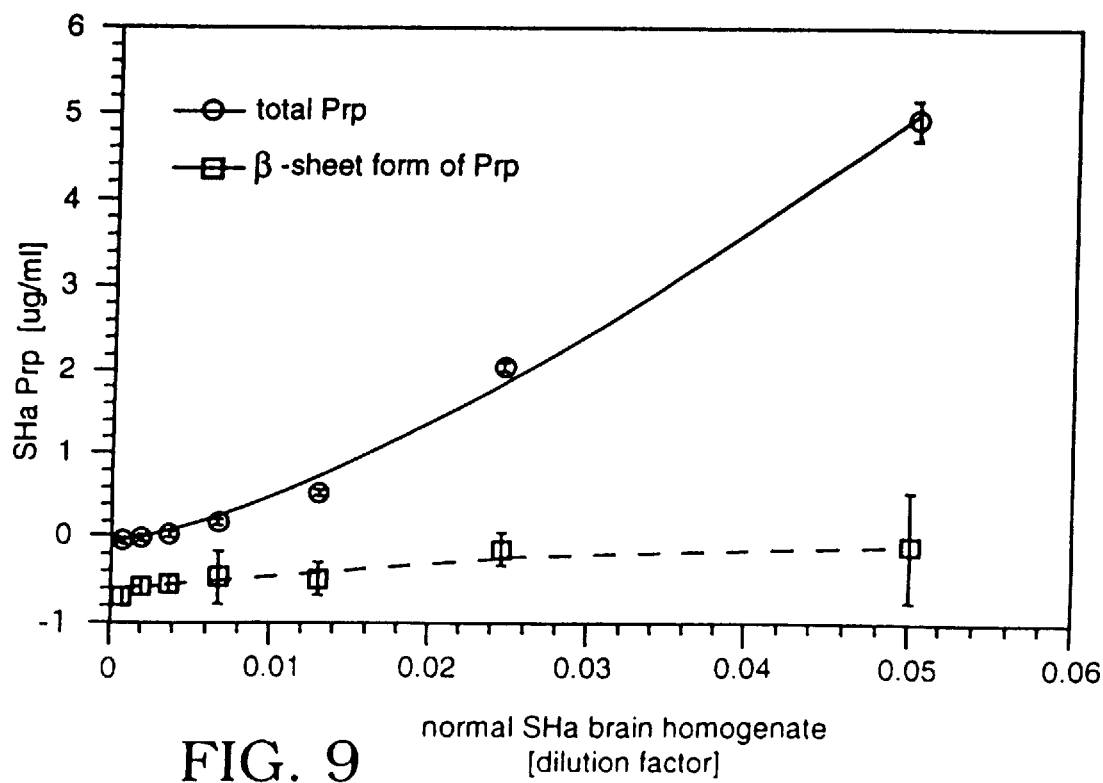
FIG. 9 is a graph showing the total amount of PrP proteins in normal hamster brains and the amount of β-sheet $PrP^{Sc}$ in both brains calculated from the model wherein the data points and bars represent average±SEM obtained from four independent measurements.
Figure 10:
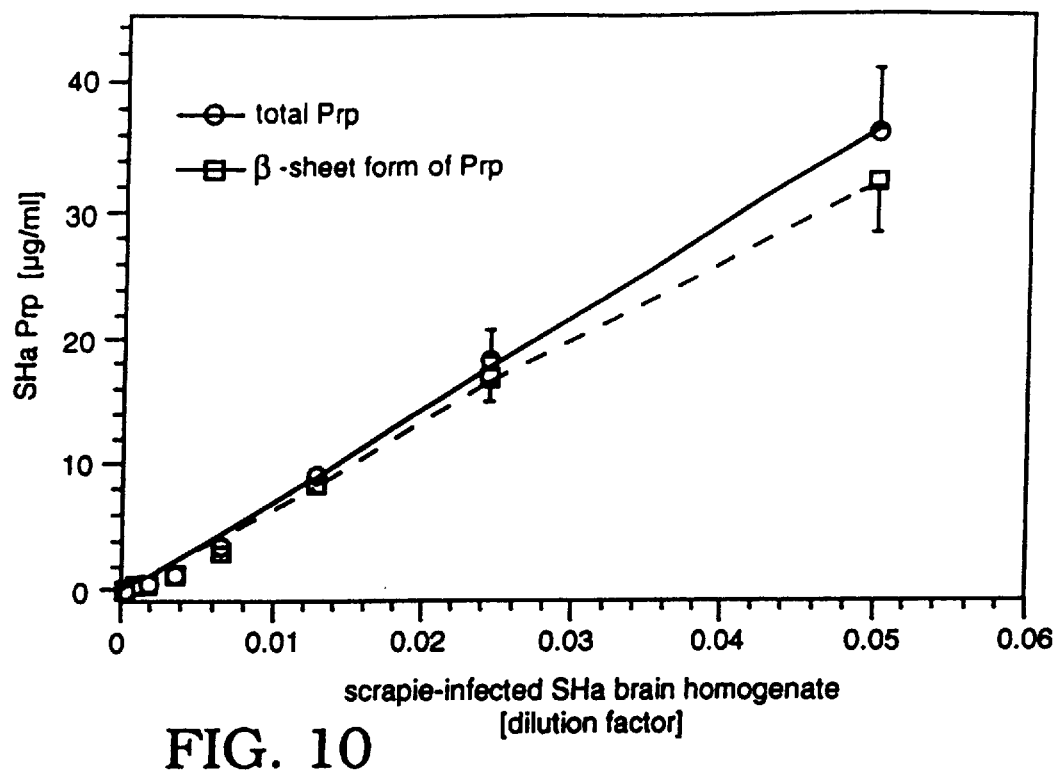
FIG. 10 is a graph showing the total amount of PrP proteins in scrapie infected hamster brains and the amount of β-sheet $PrP^{Sc}$ in both brains calculated from the model wherein the data points and bars represent average±SEM obtained from four independent measurements.
Figure 11:
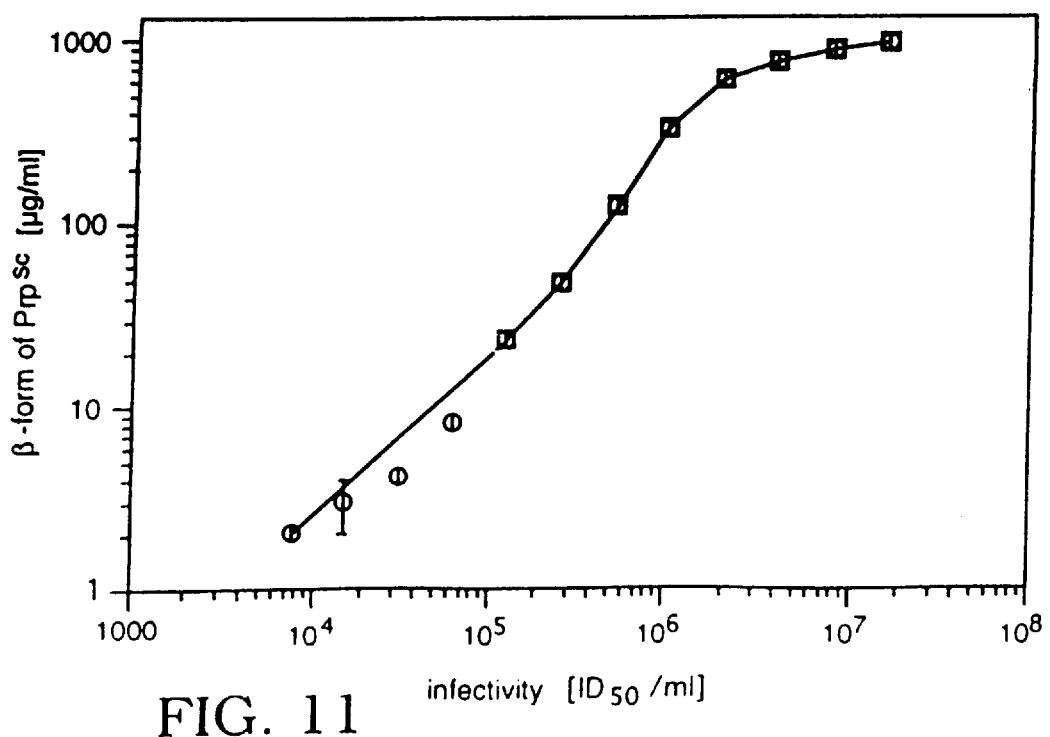
FIG. 11 is a graph showing the correlation of the infectivity and amount of β-sheet form of $SHaPrP^{Sc}$ as calculated from the direct assay and formula wherein purified $SHaPrP^{Sc}$ was sonicated in the presence of 5% $PrP^{0/0}$ mouse brain homogenate and diluted as described and wherein the data points and bars represent average±SEM obtained from four independent measurements.

This effect was further utilized to analyze PrP samples of unknown conformation where the small increase in signal of Eu-labeled 3F4 IgG after denaturation of PrP is a characteristic of α-helical conformation. By contrast, the large increase in the signal above the expected change for α-helical conformation is diagnostic of the PrP90-231 in β-sheet conformation (FIGS. 3 and 4). The results are expressed in two different forms: (1) as a ratio (FIG. 6), where index $\leq 1.8$ for recombinant SHaPrP90-231 indicates that the protein was originally in all α-helix conformation and index >1.8 indicates presence of β-sheet conformation; (2) as a formula shown herein and exemplified in Example 11, where the excess increase of signal above that expected for α-helical conformation is proportionate to the amount of SHaPrP90-231 in β-sheet conformation

Example 6

Quantitative Assay for Recombinant SHaPrP90-231 and PrP$^C$

The input/output calibration for denatured ShaPrP90-231 in both α-helical and β-sheet conformations was linear within three orders of magnitude, and provide a high degree of confidence (FIG. 5) for the assay. Also assayed was $PrP^C$, serially diluted into $PrP^{0/0}$ mouse homogenate which provided results with high degree of confidence within linearity range of 3 orders of magnitude. Next, the assay was calibrated by purified infectious $PrP^{Sc}$ in the presence of 5% $PrP^{0/0}$ brain homogenate. The calibration with $PrP^{Sc}$ provided a linear response within similar range.

Using the differential method, the ratio between the signal of denatured versus native brain $PrP^C$ was for Eu-labeled monoclonal 3F4 IgG 2.2 (FIG. 7), for polyclonal N12 and P3 1.0. The calibration for $PrP^{Sc}$ gave ratio ≧20 (FIG. 8) for 3F4 Eu-labeled IgG and >4 for N12 and P3 antibodies. By using the formulae developed shown herein, all $PrP^C$ was in full range in α-helical conformation. In contrast, the calculated amount of $PrP^{Sc}$ in infectious, β-sheet conformation was as anticipated close to the total amount of prion protein.

Example 7

Diagnosis of Prion Disease Based on Increase of Total Prion Protein Above Physiological $PrP^C$ Levels Accurate quantitative measurement of total PrP by exclusively evaluating the signal of denatured sample gave an average value of $PrP^C$ in 5% normal Syrin Hamster brain homogenates of 5.0±0.2 μg/ml (Mean±SEM) (FIG. 9). The serial dilution of scrapie (Strain Sc237)-infected hamster brain homogenate into $PrP^{0/0}$ mouse brain homogenate gave values of total PrP 36.0±4 μg/ml (FIG. 10) with broad linearity of the measurement. Because the only known condition for accumulation of prion protein is the accumulation of the infectious $PrP^{Sc}$ form, the increased levels of total PrP in the tested sample is indicative of the presence of prions. This prion assay may be used: (1) in direct mode in brain, tissue samples, body fluids or pharmaceuticals after determination of normal control values; or (2) in indirect mode by detecting the elevation of total PrP in the brain of experimental animal intracerebrally inoculated with tested tissue, body fluid or pharmaceutical sample suspected of containing prions.

Example 8

Diagnosis of Prion Disease Based on Increase of the Signal Ratio Between Denatured vs Native PrP ("Prion Index")

The ratio between antibody affinity for denatured versus native Syrian hamster brain $PrP^C$ protein is in the broad concentration range for Eu-labeled 3F4 IgG between 0.8–2.2. The ratio in the scrapie infected brain is through the full linearity range above those values (FIG. 11). The "prion index" gives a relative indicator of the presence of infectious $PrP^{Sc}$ and therefore prions. This mode of prion assay is being used: (1) in direct mode in brain, tissue samples, body fluids or pharmaceuticals after determination of the index for normal controls; or (2) in indirect mode by detecting the elevated denatured/native prion protein index in the brain of experimental animals intracerebrally inoculated with tested tissue, body fluid or pharmaceutical sample suspected from containing prions.

Example 9

Diagnosis of Prion Disease from Differential Assay by Calculating $PrP^{Sc}$ Content By using the direct assay and formulae provided here, there is no detectable amount of β-sheet form of $PrP^{Sc}$ in normal brain homogenate. Conversely, most of the total PrP in scrapie-infected hamster brain was due to the accumulation of $PrP^{Sc}$ (FIGS. 9 and 10). The correlation between the prion titer and $PrP^{Sc}$ calculated from the formula has a broad linearity and sensitivity cutoff of ~$10^3$ $ID_{50}$/ml (FIG. 11). The formula gives quantitative indicator of the presence of PrP protein in abnormal conformation which quantitatively correlates with prion titer. This mode of prion assay is used: (1) in direct mode in brain, tissue samples, body fluids or pharmaceuticals; or (2) in indirect mode, by calculating $PrP^{Sc}$ content in the brain of experimental animals intracerebrally inoculated with tested tissue, body fluid or pharmaceutical samples suspected for containing prions. After establishing a calibration curve between PrP$^{Sc}$ and prion titer, it is possible to estimate the titer directly from PrP$^{Sc}$ content.

Example 10

The Measurement of α-helix-to-β-sheet Conversion of PrP Protein in Vitro to Screen Prion Generation De Novo and Potential Disease Therapeutics

The aliquots of a 100 μg/ml solution of the α-helical form of recombinant SHaPrP90-231, or SHaPrP29–231, or corresponding recombinant or synthetic peptides of the prion protein are incubated in 20 mM Na acetate buffer, pH 5.5, for 24 hrs at 37° C. with $10^{-3}$–$10^{-5}$M concentrations of glycerol, cyclodextrins, heparin, heparin sulfate, Congo Red, cholesterol ester, dimyristoyl phosphatidylcholine. The samples are then divided into two aliquots: (1) untreated, designated native; (2) mixed with final 4M Gdn HCl and heated for 5 min at 100° C., designated denatured. Both samples are diluted 20-fold by H$_2$O and aliquots loaded on polystyrene plate activated with glutaraldehyde. The plates, incubated overnight at 5° C., were blocked with TBS, pH 7.8, containing 0.5% BSA (w/v) and 6% Sorbitol (w/v). In the next step, they were washed three time with TBS, pH 7.8 containing 0.05% (v/v) of Tween 20 and incubated with Europium-labeled 3F4 IgG. The plates were developed after additional 7 washing steps in enhancement solution provided by the Europium label supplier (Wall, Turk, Finland) and signal counted on DELFIA 1234 Fluorometer (Wallac, Turku, Finland).

The degree of conversion from α-helical to β-sheet conformation of PrP is calculated from the "prion index" or alternatively from the formulae provided herein. Some compounds which inhibit the conversion by apparently stabilizing the native-like conformation of prion protein may have therapeutic potential in vivo.

Example 11

The assay method is demonstrated on the following example with scrapie-infected Syrian hamster brain homogenate, diluted 4-fold into PrnP$^{0/0}$ mouse brain homogenate:

a) Each plate is calibrated with an inner standard consisting from five dilution points of denatured SHaPrP90-231. The time-resolved fluoresence (TRF) of total PrP is developed with Eu-labeled 3F4 IgG and the time-resolved fluoresence values are plotted as a function of PrP concentration (FIG. 4). The data are fit within a linear or polynomial equation using the least square method and best function is selected for the calculation of denatured PrP:

$$\text{PrP } [\mu g/ml] = -0.22935 + 0.00026567 * [TRF] + 0.0000000012255 * [TRF]^2 \quad (1)$$

b) On the rest of the plate, native and denatured aliquots of scrapie-infected Syrian hamster brain homogenate, diluted 4-fold, and crosslinked to the plastic support were incubated with Eu-labeled 3F4 IgG. The total PrP content is calculated according to the above formula from the fluorescence signal of denatured sample:

| scrapie infected brain homogenate concentration [%] | native TRF [cpm] | denatured TRF [cpm] | PrP$^{C+Sc}$ [μg/ml] |
|---|---|---|---|
| 5 | 4214 | 109814 | 43.7 |
| 1.25 | 1381 | 30804 | 9.1 |
| 0.3125 | 1070 | 11240 | 2.9 | c) The ratio of the fluorescence signals between denatured and native samples is calculated:

| scrapie infected brain homogenate concentration [%] | native TRF [cpm] | denatured TRF [cpm] | denatured/ native ratio |
|---|---|---|---|
| 5 | 4214 | 109814 | 26.1 |
| 1.25 | 1381 | 30804 | 22.3 |
| 0.3125 | 1070 | 11240 | 10.5 |

The normal value of PrP$^C$ determined from normal hamster brain homogenate is 2.2; the values over 2.2 are considered abnormal and indicate the presence of PrP$^{Sc}$.

d) The excess of fluoresence signal over that expected for α-helical PrP in the transition from native to denatured state is a measure of the amount of PrP$^{Sc}$ and is calculated according the formulae provided:

$$\Delta F_{\beta\ n \to d} = F_d - (F_n * f_{\alpha\ n \to d}) \quad (2)$$

where f=is the maximum value of the factor for the fluorescence signal in the transition from native to denatured state of PrP$^C$; F$_d$ is the fluorescence of denatured sample; and F$_n$ is the fluorescence of native sample. The amount of PrP$^{Sc}$ is then calculated from $\Delta F_{\beta\ n \to d}$ and equation (1):

| scrapie infected brain homogenate concentration [%] | $\Delta TRF_{\beta n \to d}$ [cpm] | PrP$^{Sc}$ [μg/ml] |
|---|---|---|
| 5 | 100543.2 | 38.9 |
| 1.25 | 27765.8 | 8.1 |
| 0.3125 | 8886 | 2.2 |

The positive value calculated for the β-sheet form of prion protein indicates the presence of PrP$^{Sc}$.

We claim:

1. An assay method, comprising:

providing a sample suspected of containing a PrP protein which assumes a first conformation and a second, disease related conformation;

dividing the sample into a first portion and a second portion;

contacting the first portion with a labelled antibody which binds to the PrP protein in its first conformation with a higher degree of affinity than it binds to the PrP protein in its second, disease related conformation;

treating the second portion in a manner which causes any PrP protein in the second, disease related conformation to assume a different conformation which conformation has a higher degree of affinity for the labelled antibody as compared to the affinity for the PrP protein in the second disease related conformation;

contacting the second portion with the labelled antibody;

determining the level of binding of labelled antibody to PrP protein in the first portion;

determining the level of binding of labelled antibody to PrP protein in the second portion; and comparing the level of binding of labelled antibody to PrP protein in the first portion with the level in the second portion and thereby determining whether the sample comprised PrP protein in the disease related second conformation.

2. The method of claim 1, further comprising:

binding PrP protein of the first portion to a first solid support surface; and binding PrP protein of the second portion to a second solid support surface.

3. The method of claim 1, wherein the treating is carried out by subjecting the second portion to a treatment selected from the group consisting of heat, pressure and chemical exposure in order to convert at least 2% of any PrP protein in the second disease related conformation to the different conformation.

4. The method of claim 1, wherein the labelled antibody has at least four times greater affinity for the PrP protein in the first conformation than for the PrP protein in the second conformation.

5. The method of claim 1, wherein the labelled antibody has at least fifteen times greater affinity for the PrP protein in the first conformation than for the PrP protein in the second conformation.

6. The method of claim 1, wherein the labelled antibody has at least thirty times greater affinity for the PrP protein in the first conformation than for the PrP protein in the second conformation.

7. An assay method, comprising:

providing a sample suspected of containing a PrP protein which assumes a first conformation and a second, disease related conformation;

treating the sample in a manner which causes an PrP protein in the second, disease related conformation to change its conformation to a different conformation having a higher binding affinity to a labelled antibody than the level of binding of said labelled antibody to said second, disease related conformation;

contacting the treated sample with said labelled antibody which binds to the PrP protein in its first conformation and different conformation with a higher degree of affinity than it binds to the PrP protein in its second, disease related conformation;

determining the level of binding of labelled antibody to PrP protein in the sample;

comparing the level of labelled antibody binding in the sample to a previously established standard level of binding to a treated standard, which treated standard prior to treatment contains a known amount of the PrP protein in (i) the first conformation and (ii) in the second, disease related conformation, and;

determining the probablilty of the sample containing PrP protein in the second, disease related conformation based on the comparison.

8. The method of claim 7, wherein the level of binding of labelled antibody to PrP protein is determined using flow cytometry.

9. The method of claim 7, further comprising:

binding PrP protein of the sample to a solid support surface.

10. The method of claim 7, wherein the standard is obtained from previous measurements of the level of PrP protein in equivalent samples from normal, non-diseased individuals.

11. The method of claim 7, wherein the standard is obtained from previous measurements of the level of the PrP protein in equivalent samples from individuals diagnosed with a disease associated with the second, disease related conformation.

12. An assay method, comprising:

providing a sample suspected of containing a PrP protein which assumes a first conformation and a second, disease related conformation;

dividing the sample into a first portion and a second portion;

contacting the first portion with a labelled antibody which binds to the PrP protein in its first conformation with a higher degree of affinity than it binds to the PrP protein in its second, disease related conformation;

treating the second portion in a manner which causes any PrP protein in the second, disease related conformation to assume a different conformation which conformation has a higher degree of affinity for the labelled antibody as compared to the affinity for the PrP protein in the second disease related conformation;

contacting the second portion with the labelled antibody;

determining the levels of binding of labelled antibody to PrP protein in the first portion;

determining the level of binding of labelled antibody to PrP protein in the second portion;

adjusting the determined level of binding of labelled antibody to PrP protein in the second portion to compensate for increasing the affinity of the PrP protein in the first conformation for the antibody resulting from the treating;

subtracting the level of binding of labelled antibody protein in the first portion from the adjusted level of binding of labelled antibody in the second portion to obtain a differential; and applying the differential to the formulae below wherein the differential is represented by the symbol Δ

$$[PrP] {\sim} \Delta F_{\beta \to d} = F_d - (F_n * f_{\alpha n \to d})$$

wherein each of the above variables is provided below:

F—any detectable signal;

$F_n$—signal of protein in native conformation;

$F_{n\alpha}$ and $F_{n\beta}$—signals of native non-disease and disease conformations, respectively;

$F_d$—signal of treated protein;

$F_{d\alpha}$ and $F_{d\beta}$—are the signals of treated non-disease and disease conformations;

$\Delta F_{n \to d}$—increase of signal in the transition from native to treated state;

$\Delta F_{\alpha n \to d}$—increase in the signal of non-disease conformation in the transition from native to treated state;

$\Delta F_{\beta n \to d}$—increase in the signal of disease conformation in the transition from native to treated state;

$f_{\alpha n \to d}$—correlation factor for the transition from native to treated state of non-disease conformation;

$[PrP_\beta]$—concentration of protein in disease conformation;

∼—is proportional to;

*—is multiply by.

13. The method of claim 1, wherein levels of binding of labelled antibody to PrP protein are determined using flow cytometry.

14. The method of claim 12, wherein levels of binding of labelled antibody to PrP protein are determined using flow cytometry, and the labelled antibody is fluorescence labelled 3F4 IgG.

15. The method of claim 1, wherein the labelled antibody is Europium-labelled 3F4 IgG.

16. The method of claim 7, wherein the labelled antibody is Europium-labelled 3F4 IgG.

17. The method of claim 1, wherein levels of binding of labelled antibody to PrP protein are determined using time-resolved, dissociation-enhanced fluorescence.

18. The method of claim 7, wherein levels of binding of labelled antibody to PrP protein are determined using time-resolved, dissociation-enhanced fluorescence.

19. The method of claim 12, wherein levels of binding of labelled antibody to PrP protein are determined using time-resolved, dissociation-enhanced fluorescence.

20. The method of claim 1, further comprising:
adjusting the determined level of binding of labelled antibody to PrP protein in the second portion to compensate for increasing the affinity of the PrP protein in the first conformation for the antibody resulting from the treating.

* * * * *

UNITED STATES PATENT AND TRADEMARK OFFICE
CERTIFICATE OF CORRECTION

PATENT NO: 5,891,641
DATED: April 6, 1999
INVENTOR(S): Stanley B. Prusiner; Jiri G. Safar It is certified that error appears in the above-identified patent and that said Letters Patent is hereby corrected as shown below:

Column 1, line 3, add the following:

--Research described here was conducted in part with Government support under Grant No. AG08967, awarded by the National Institutes of Health. The Government may have certain rights in this invention.--

Signed and Sealed this

Seventh Day of September, 1999

Attest:

Q. TODD DICKINSON

Attesting Officer

Acting Commissioner of Patents and Trademarks